US008449473B2

(12) United States Patent  
Varney et al.

(10) Patent No.: US 8,449,473 B2
(45) Date of Patent: *May 28, 2013

(54) GAS SENSOR

(75) Inventors: Mark Sinclair Varney, Bishopstoke (GB); Michael Garrett, Woking (GB); Deryk John Peter Williams, Woking (GB)

(73) Assignee: Anaxsys Technology Limited, Send (GB)

( * ) Notice: Subject to any disclaimer, the term of this patent is extended or adjusted under 35 U.S.C. 154(b) by 1308 days.

This patent is subject to a terminal disclaimer.

(21) Appl. No.: 12/081,113

(22) Filed: Apr. 10, 2008

(65) Prior Publication Data

US 2008/0262370 A1    Oct. 23, 2008

Related U.S. Application Data

(63) Continuation-in-part of application No. PCT/GB2007/003957, filed on Oct. 17, 2007.

(30) Foreign Application Priority Data

Oct. 18, 2006 (GB) ................................. 0620711.2
May 17, 2007 (GB) ................................. 0709439.4

(51) Int. Cl.
*A61B 5/08* (2006.01)
(52) U.S. Cl.
USPC ............................ 600/532; 600/538; 600/543
(58) Field of Classification Search
None
See application file for complete search history.

(56) References Cited

U.S. PATENT DOCUMENTS

| 3,860,498 | A | * | 1/1975 | Jones ............................. 205/784 |
| 4,298,347 | A | | 11/1981 | Walsh | |
| 4,347,732 | A | | 9/1982 | Leary | |
| 4,377,446 | A | | 3/1983 | Albery | |
| 4,795,543 | A | | 1/1989 | Stetter et al. | |
| 5,131,990 | A | | 7/1992 | Kulwicki et al. | |
| 5,309,921 | A | | 5/1994 | Kisner et al. | |
| 5,364,797 | A | * | 11/1994 | Olson et al. ..................... 436/501 |
| 5,418,131 | A | | 5/1995 | Butts | |
| 5,531,808 | A | | 7/1996 | Ojo et al. | |
| 5,585,559 | A | | 12/1996 | Hata | |
| 5,606,264 | A | | 2/1997 | Licari et al. | |
| 5,716,506 | A | | 2/1998 | Maclay et al. | |
| 5,772,863 | A | | 6/1998 | Shoemaker et al. | |
| 6,014,890 | A | | 1/2000 | Breen | |
| 6,038,913 | A | | 3/2000 | Gustafsson et al. | |
| 6,069,013 | A | | 5/2000 | Plog et al. | |
| 6,277,523 | B1 | | 8/2001 | Giron | |
| 6,454,923 | B1 | | 9/2002 | Dodgson et al. | |
| 6,790,178 | B1 | | 9/2004 | Mault et al. | |
| 2003/0131653 | A1 | | 7/2003 | Bair, III et al. | |
| 2004/0236240 | A1 | | 11/2004 | Kraus et al. | |
| 2006/0104141 | A1 | | 5/2006 | Jo | |
| 2007/0021681 | A1 | | 1/2007 | Sokoloff | |
| 2007/0056352 | A1 | | 3/2007 | Birkhofer et al. | |

FOREIGN PATENT DOCUMENTS

| DE | 19732025 | 1/1999 |
| DE | 199 41 586 A1 | 9/1999 |
| DE | 10228088 | 3/2004 |
| DE | 10330742 | 1/2005 |
| EP | 0044806 | 1/1982 |
| EP | 0293230 | 11/1988 |
| EP | 0299780 | 1/1989 |
| EP | 0699414 | 3/1996 |
| EP | 0856734 | 8/1998 |
| EP | 1005904 | 6/2000 |
| EP | 1304565 | 4/2003 |
| EP | 1653230 | 5/2006 |
| GB | 2184549 | 6/1987 |
| GB | 2287543 | 9/1995 |
| GB | 2312961 | 11/1997 |
| GB | 2316178 | 2/1998 |
| GB | 2403295 | 12/2004 |
| GB | 2417083 | 2/2006 |
| JP | 06-018475 | 1/1994 |
| JP | H09-16272 | 1/1997 |
| WO | WO 84/04595 | 11/1984 |
| WO | WO 2004/001407 | 12/2003 |
| WO | 2004/030132 | 4/2004 |
| WO | WO 2005/059536 | 6/2005 |
| WO | 2006/016188 | 2/2006 |
| WO | WO 2006/016188 | 2/2006 |
| WO | WO2006/045628 | 5/2006 |
| WO | WO 2007/031769 | 3/2007 |
| WO | WO2007/080381 | 7/2007 |

(Continued)

OTHER PUBLICATIONS

Smith et al. Selected Ion Flow Tube Mass Spectrometry (SIFT-MS) for On-Line Trace Gas Analysis. Mass Spectrometry Reviews 2005, vol. 24, pp. 661-700.*
You et al. Expiratory capnography in asthma. European Respiratory Journal 1994, vol. 7, pp. 318-323.*
International Search Report for PCT/GB2009/050352.
Baglio, V. et al., "Zeolite-based composite membranes for high temperature direct methanol fuel cells," Journal of Applied Electrochemistry, Feb. 1, 2005, pp. 207-212, vol. 35, No. 2, Kluwer Academic Publishers, DO.
Kalkan et al., "A Rapid-Response, High-Sensitivity Nanophase Humidity Sensor for Respiratory Monitoring," IEEE Electron Device Letters, IEEE Service Center, Aug. 1, 2004, pp. 526-528, New York, NY, US.

(Continued)

*Primary Examiner* — Louise Humphrey
(74) *Attorney, Agent, or Firm* — McDonnell Boehnen Hulbert & Berghoff LLP

(57) ABSTRACT

A method of determining the respiratory function of a subject is disclosed, the method comprising measuring the concentration of water vapor in the gas stream exhaled by the subject, and from the measured water vapor concentration determining the respiratory function of the subject. Mathematical techniques for analyzing the data obtained from the measurement of concentrations of gaseous components in an exhaled gas stream are also disclosed and their use in determining the lung function of a subject.

16 Claims, 16 Drawing Sheets

FOREIGN PATENT DOCUMENTS

| | | |
|---|---|---|
| WO | WO 2008/009951 | 1/2008 |
| WO | WO 2008/009980 | 1/2008 |
| WO | WO 2008/047115 | 4/2008 |

OTHER PUBLICATIONS

Tatara et al., "An Apnea Monitor Using a Rapid-Response Hygrometer," Journal of Clinical Monitoring, Jan. 1, 1997, pp. 5-9, vol. 3.
International Search Report for PCT/GB2007/002748.
International Search Report for PCT/GB2007/002807.
International Search Report for PCT/GB2005/003196.
International Search Report for PCT/GB2006/003432.
International Search Report for PCT/GB2007/003957.
Search Report for GB0418078.2.
Search Report for GB0518812.3.
Search Report for GB0614504.9.
Search Report for GB0614505.6.
Search Report for GB0620711.2.
Bearzotti et al., "Relative humidity and Alcohol sensors based on mesoporous silica thin films synthesised from block copolymers", Sensors and Actuators B, Elsevier Sequoia S.A., Lausanne, CH, vol. 95, No. 1-3, Oct. 15, 2003, pp. 107-110 (4 pages).
Creasey et al., "The Development of a Thick-Film Electrochemical Sensor and Instrumentation for In-Situ Determination of Carbon Dioxide Partial Pressure ($pCO_2$) in the Marine Environment", Electronic Engineering in Oceanography, 1994, Sixth International Conference on Cambridge, UK, London, pp. 124-128 (5 pages).
Innocenzi et al., "Electrical and structural characterisation of mesoporous silica thin films as humidity sensors", Sensors and Actuators B., Elsevier Sequoia S.A. Lausanne, CH, vol. 76, No. 1-3, Jun. 1, 2001, pp. 299-303 (5 pages).
Mortimer et al., "AC impedance characteristics of solid-state planar electrochemical carbon monoxide sensors with Nafion® as solid polymer electrolyte", Electrochimica Acta, Elsevier Science Publishers, Barking, GB, vol. 47, No. 20, Aug. 5, 2002, pp. 3383-3387 (5 pages).
Mousty, "Sensors and biosensors based on clay-modified electrodes—new trends", Applied Clay Science, Elsevier Science, NL., vol. 27, No. 3-4, Dec. 2004, pp. 159-177 (19 pages).
Qian et al., "A hydrogen biosensor made of clay, poly(butylviologen), and hydrogenase sandwiched on a glass carbon electrode", Biosensors & Bioelectronics, Elsevier Science Publishers, Barking, GB, vol. 17, No. 9, Sep. 2002, pp. 789-796 (8 pages).
Otagawa et al., "Planar Microelectrochemical Carbon Monoxide Sensors", Sensors and Actuators B, Elsevier Sequoia S.A. Lausanne, CH, vol. 1, No. 1-6, Jan. 1990, pp. 319-325 (7 pages).
Spanel et al., "On-line measurement of the absolute humidity of air, breath and liquid headspace samples by selected ion flow tube mass spectrometry", Rapid Communications in Mass Spectrometry, vol. 15, No. 8, Apr. 30, 2001, pp. 563-569 (7 pages).
Tricoli et al., "Zeolite-Nafion composites as ion conducting membrane materials", Electrochimica Acta, Elsevier Science Publishers, Barking, GB, vol. 48, No. 18, Aug. 1, 2003, pp. 2625-2633 (9 pages).
Van Der Wal et al., "Extremely stable Nafion based carbon monoxide sensor", Sensors and Actuators B, Elsevier Sequoia S.A. Lausanne, CH, vol. 35, No. 1, Sep. 1996, pp. 119-123 (5 pages).
Wang et al., "Electrical sensing properties of silica aerogel thin films to humidity", Thin Solid Films, Elsevier-Sequoia S.A. Lausanne, CH, vol. 496, No. 2, Feb. 21, 2006, pp. 658-664 (7 pages).
Yasuda et al., "Electrochemical carbon monoxide sensor with a Nafion® film", Reactive & Functional Polymers, Elsevier Science Publishers BV, NL, vol. 41, No. 1-3, Jul. 15, 1999, pp. 235-243 (9 pages).

* cited by examiner

GAS SENSOR

CROSS-REFERENCE TO RELATED APPLICATIONS

This application is a Continuation-In-Part of International Patent Application No. PCT/GB2007/003957, filed Oct. 17, 2007, which claims priority from Great Britain Patent Application Nos. 0620711.2, filed Oct. 18, 2006, and 0709439.4, filed May 17, 2007. The entire contents of these applications are hereby incorporated by reference in their entirety.

The present invention is related to a sensor for detecting gaseous substances, in particular a sensor for detecting the presence of substances in a stream of gas exhaled by a patient or subject. The sensor is particularly suitable for, but not limited to, the analysis of the carbon dioxide and/or water content of the gas stream. The sensor finds particular use as a capnographic sensor for detecting and measuring the concentration of gases, such as carbon dioxide, in the exhaled breath of a person or animal, to thereby provide an indication of the condition of the respiratory system of a patient or subject and to assist in the identification and diagnosis of respiratory ailments or illness. In a particularly preferred embodiment, the sensor is employed in the determination of the water vapour content of a gas stream exhaled by a subject and to the use of the results of the same for indicating the lung function of the subject.

The analysis of the carbon dioxide content of the exhaled breath of a person or animal is a valuable tool in assessing the health of the subject. In particular, measurement of the carbon dioxide concentration allows the extent and/or progress of various pulmonary and/or respiratory diseases to be estimated, in particular asthma and chronic obstructive lung disease (COPD).

Carbon dioxide can be detected using a variety of analytical techniques and instruments. The most practical and widely used analysers use spectroscopic infra-red absorption as a method of detection, but the gas may also be detected using mass spectrometry, gas chromatography, thermal conductivity and others. Although most analytical instruments, techniques and sensors for carbon dioxide measurement are based on the physicochemical properties of the gas, new techniques are being developed which utilise electrochemistry, and an assortment of electrochemical methods have been proposed. However, it has not been possible to measure carbon dioxide ($CO_2$) gas directly using electrochemical techniques. Indirect methods have been devised, based on the dissolution of the gas into an electrolyte with a consequent change in the pH of the electrolyte. Other electrochemical methods use high temperature catalytic reduction of carbon dioxide. However, these methods are generally very expensive, cumbersome to employ and often display very low sensitivities and slow response times. These drawbacks render them inadequate for analyzing breath samples, in particular in the analysis of tidal breathing.

A more recently applied technique is to monitor a specific chemical reaction in an electrolyte that contains suitable organometallic ligands that chemically interact following the pH change induced by the dissolution of the carbon dioxide gas. The pH change then disturbs a series of reactions, and the carbon dioxide concentration in the atmosphere is then estimated indirectly according to the change in the acid-base chemistry.

Carbon dioxide is an acid gas, and interacts with water, and other (protic) solvents. For example, carbon dioxide dissolves in an aqueous solution according to the following reactions:

  (1)

  (2)

  (3)

It will be appreciated that, as more carbon dioxide dissolves, the concentration of hydrogen ions ($H^+$) increases.

The use of this technique for sensing carbon dioxide has the disadvantage that when used for gas analysis in the gaseous phase the liquid electrolyte must be bounded by a semi-permeable membrane. The membrane is impermeable to water but permeable to various gases, including carbon dioxide. The membrane must reduce the evaporation of the internal electrolyte without seriously impeding the permeation of the carbon dioxide gas. The result of this construction is an electrode which works well for a short period of time, but has a long response time and in which the electrolyte needs to be frequently renewed.

WO 04/001407 discloses a sensor comprising a liquid electrolyte retained by a permeable membrane, which overcomes some of these disadvantages. However, it would be very desirable to provide a sensor that does not rely on the presence and maintenance of a liquid electrolyte.

U.S. Pat. No. 5,772,863 discloses a sensor for oxygen and carbon dioxide gases having a plurality of layers comprising an alumina substrate, a reference electrode source of anions, a lower electrical reference electrode of platinum coupled to the reference source of anions, a solid electrolyte containing tungsten and coupled to the lower reference electrode, a buffer layer for preventing the flow of platinum ions into the solid electrolyte and an upper electrode of catalytic platinum.

GB 2,287,543 A discloses a solid electrolyte carbon monoxide sensor having a first cavity formed in a substrate, communicating with a second cavity in which a carbon monoxide adsorbent is located. An electrode detects the partial pressure of oxygen in the carbon monoxide adsorbent. The sensor of GB 2,287,543 is very sensitive to the prevailing temperature and is only able to measure low concentrations of carbon monoxide at low temperatures with any sensitivity. High temperatures are necessary in order to measure carbon monoxide concentrations that are higher, if complete saturation of the sensor is to be avoided. This renders the sensor impractical for measuring gas compositions over a wide range of concentrations.

GB 2,316,178 A discloses a solid electrolyte gas sensor, in which a reference electrode is mounted within a cavity in the electrolyte. A gas sensitive electrode is provided on the outside of the solid electrolyte. The sensor is said to be useful in the detection of carbon dioxide and sulphur dioxide. However, operation of the sensor requires heating to a temperature of at least 200° C., more preferably from 300 to 400° C. This represents a major drawback in the practical applications of the sensor.

Sensors for use in monitoring gas compositions in heat treatment processes are disclosed in GB 2,184,549 A. However, as with the sensors of GB 2,316,178, operation at high temperatures (up to 600° C.) is disclosed and appears to be required.

Accordingly, there is a need for a sensor that does not rely on the presence of an electrolyte in the liquid phase or high temperature catalytic method, that is of simple construction and may be readily applied to monitor gas compositions at ambient conditions.

EP 0 293 230 discloses a sensor for detecting acidic gases, for example carbon dioxide. The sensor comprises a sensing electrode and a counter electrode in a body of electrolyte. The electrolyte is a solid complex having ligands that may be displaced by the acidic gas. A similar sensor arrangement is disclosed in U.S. Pat. No. 6,454,923.

A particularly effective sensor is disclosed in pending international application No. PCT/GB2005/003196. The sensor comprises a sensing element disposed to be exposed to the gas stream, the sensing element comprising a working electrode; a counter electrode; and a solid electrolyte precursor extending between and in contact with the working electrode and the counter electrode; whereby the gas stream may be caused to impinge upon the solid electrolyte precursor such that water vapour in the gas stream at least partially hydrates the precursor to form an electrolyte in electrical contact with the working electrode and the counter electrode.

It would be advantageous if the speed of response of the known sensors could be increased, while at the same time maintaining the accuracy of the sensors. In this respect, it is to be noted that carbon dioxide, a particularly preferred target molecule, in particular in the analysis of exhaled breath of patients and subjects, is a relatively large molecule, with a consequently low rate of mass transport to the sensing components of sensing devices.

The gas stream exhaled by a person or animal contains a range of components, including carbon dioxide and water vapour. It has been found that a strong relationship exists between the water vapour content of the exhaled gas stream and the carbon dioxide content of the gas stream.

Accordingly, in a first aspect, the present invention provides a method for the determination of the carbon dioxide content of an exhaled gas stream, the method comprising:
  measuring the water vapour content of the exhaled gas stream; and
  determining the concentration of carbon dioxide in the exhaled gas stream from the measured water vapour content.

As noted above, it has been found that as a result of respiration in the respiratory tract of a human or animal the concentration of carbon dioxide present in the exhaled gas stream is closely related to that of water, at a given temperature. Typically, the gas stream exhaled by a human contains approximately 79% nitrogen, 15% oxygen, 5% carbon dioxide and 2% water vapour, by volume. Thus, the ratio of carbon dioxide to water vapour in the exhaled gas is typically 2.5:1.

The ability to determine carbon dioxide concentration of exhaled gas streams from the detection and measurement of the water vapour content offers a number of advantages. First, of the individual components making up an exhaled gas stream, water is the only sub-critical gas component present and is thus readily condensable in a sensor. Further, as the water molecule is significantly smaller than the carbon dioxide molecule, its rate of diffusion and mass transfer is correspondingly faster, giving the potential for providing a sensor that has a fast response time. This is of importance when designing a sensor to be used on a regular basis by subjects, such as patients wishing to detect a respiratory disorder, for example an asthmatic wishing to identify the onset of an asthma attack.

The sensor used for measuring the concentration of the water vapour in the exhaled gas stream may be sensitive to water vapour alone. Alternatively, the sensor may be one that is sensitive to both water vapour and carbon dioxide, account of which is taken when processing the output of the sensor to determine the carbon dioxide concentration.

In the human or animal respiratory system, gas may be inhaled and exhaled either through the nasal passages or through the mouth. The nasal passages provide a mechanism for heat exchange and moisture exchange with the passing gas stream, which functions are not performed to the same extent by the structures of the mouth. Due to the different structures and their different functions, the composition of gas exhaled through the mouth will differ from that of a gas stream exhaled through the nose. In the present invention, it is preferred that the method of determining carbon dioxide concentration is performed in a gas stream exhaled through the mouth, in order to provide a result for use the assessment of respiratory function of the subject.

The method may employ any suitable technique for determining the moisture content of the exhaled gas stream. Suitable methods will be known to the person skilled in the art. One technique for the measurement of the absolute humidity of exhaled gas streams is selected ion flow tube mass spectrometry (SIFT-MS), as disclosed by P. Spanel and D. Smith, 'On-line measurement of the absolute humidity of air, breath and liquid headspace samples by selected ion flow tube mass spectrometry', Rapid Communications in Mass Spectrometry, 2001, 15, pages 563 to 569.

In a further aspect, the present invention provides a sensor for determining the concentration of carbon dioxide in an exhaled gas stream, the sensor comprising:
  means for determining the concentration of water vapour in the exhaled gas stream; and
  means for calculating the concentration of carbon dioxice in the exhaled gas stream from the measured water vapour concentration.

As noted above, the sensor may employ any suitable technique for determining the concentration of water vapour in the exhaled gas stream. In a preferred embodiment, the present invention employs an electrochemical sensor. Suitable electrochemical sensors are known in the art and include sensors disclosed in the prior art documents discussed hereinbefore. In one embodiment, the electrochemical sensor comprises:
  a sensing element disposed to be exposed to the gas stream, the sensing element comprising:
    a working electrode; and
    a counter electrode.

The electrodes may be uncoated and exposed directly to the gas stream. Alternatively, the electrodes may be coated with a suitable material to provide an electrochemical conductive path between the electrodes when water vapour is present in the gas stream.

In one preferred sensor, the electrodes are coated with a layer of ion exchange material extending between the working electrode and the counter electrode; whereby contact of the ion exchange layer with the gas stream forms an electrical contact between the working and counter electrodes.

In the present specification, references to an ion exchange material are to a material having ion exchange properties, such that contact with the components of a gas stream results in a change in the conductivity of the layer between the electrodes. The ion exchange material acts as the support medium for electrical conduction to occur, as it allows a hydrated ionic layer to form between the electrodes. The layer of ion exchange material provides a medium that is highly controllable and hydrates uniformly to provide a suitable medium for conduction to occur.

Suitable ion exchange materials for use in the sensor of the present invention are those having a high proton conductivity, good chemical stability, and the ability to retain sufficient mechanical integrity. The ion exchange material should have a high affinity for the species present in the gas stream being analysed, in particular for the various components that are present in the exhaled breath of a subject or patient.

Suitable ion exchange materials are known in the art and are commercially available products.

Particularly preferred ion exchange material are the ionomers, a class of synthetic polymers with ionic properties. A particularly preferred group of ionomers are the sulphonated tetrafluoroethylene copolymers. An especially preferred ionomer from this class is Nafion®, available commercially from Du Pont. The sulphonated tetrafluoroethylene copolymers have superior conductive properties due to their proton conducting capabilities. The sulphonated tetrafluoroethylene copolymers can be manufactured with various cationic conductivities. They also exhibit excellent thermal and mechanical stability and are biocompatible, thus making them suitable materials for use in the controlled electrode coating.

Other suitable ion exchange materials include polyether ether ketones (PEEK), poly(arylene-ether-sulfones) (PSU), PVDF-graft styrenes, acid doped polybenimidazoles (PBI) and polyphosphazenes.

The ion exchange material may be present in the sensor in the dry state, in which case the material will require the addition of water, for example as water vapour present in the gas stream. This is the case when the sensor is used to analyse the exhaled breath of a human or animal, where water vapour in varying amounts is present. Alternatively, the ion exchange material may be present with water in a saturated or partially-saturated state, in which case a dry gas stream may be analysed. In such a case, the output of the sensor will change in response to a change in the conductance of the ion exchange material, due to the dissolution of ions in the water present.

The thickness of the ion exchange material will determine the response of the sensor to changes in the composition of the gas stream in contact with the ion exchange layer. To minimize internal resistance within the sensor, it is preferred to use an ultra thin ion exchange layer.

The ion exchange layer may comprise a single ion exchange material or a mixture of two or more such materials, depending upon the particular application of the sensor.

The ion exchange layer may consist of the ion exchange material in the case the material exhibits the required level of chemical and mechanical stability and integrity for the working life of the sensor. Alternatively, the ion exchange layer may comprise an inert support for the ion exchange material. Suitable supports include oxides, in particular metal oxides, including aluminium oxide, titanium oxide, zirconium oxides and mixtures thereof. Other suitable supports include oxides of silicon and the various natural and synthetic clays.

In a second preferred embodiment, the electrodes of the sensor are coated in a layer of mesoporous material extending between the working electrode and the counter electrode; whereby contact of the mesoporous layer with the gas stream forms an electrical contact between the working and counter electrodes.

In the present specification, references to a mesoporous material are to a material having pores in the range of from 1 to 75 nm, more particularly in the range of from 2 to 50 nm. The mesoporous material acts as the support medium for electrical conduction to occur, as it allows a temporary hydrated ionic layer to form across the electrodes. The layer of mesoporous material provides a medium that is highly controllable and hydrates uniformly to provide a suitable medium for conduction to occur.

Suitable mesporous materials for use in the sensor of the present invention include metal oxides, in particular oxides of metals from Group IV of the Periodic Table of the Elements, in particular oxides of titanium or zirconium. A particularly preferred metal oxide is titanium oxide, including the titanates. Alternative mesoporous materials of use are synthetic clays, of particular preference due to the inherent layered nature of the clays. Laponite is a synthetic layered silicate with a structure resembling that of the natural clay mineral, hectonite. When added to water with stirring it will disperse rapidly into nanoparticles. It is cost effective, heat stable, thixotropic and can retain levels of hydration. Laponite is of special interest because of its single ion conducting character, where concentration polarization can be minimised. Hydrotalcite-like compounds are known also as layered double hydroxides or anionic clays. These compounds have a layered crystal structure composed of positively charged hydroxide layers and interlayers containing anions and water molecules. These compounds exhibit anion-exchange properties and can recover the layered crystal structure during rehydration.

The mesoporous material may be present in the sensor in the dry state, in which case the material will require the addition of water, for example as water vapour present in the gas stream. Alternatively, the mesoporous material may be present with water in a saturated or partially-saturated state.

The thickness of the mesoporous material will determine the response of the sensor to changes in the composition of the gas stream in contact with the mesoporous layer. To minimize internal resistance within the sensor, it is preferred to use an ultra thin mesoporous layer.

The mesoporous material may comprise a binder, in particular a conductive (ion exchanger type) binder. Suitable conductive binders include ionomers, a class of synthetic polymers with ionic properties. A particularly preferred group of ionomers are the sulphonated tetrafluoroethylene copolymers. An especially preferred ionomer from this class is Nafion®, available commercially from Du Pont. The sulphonated tetrafluoroethylene copolymers have superior conductive properties due to their proton conducting capabilities. The pores in the mesoporous material allow movement of cations but the membranes do not conduct anions or electrons. The sulphonated tetrafluoroethylene copolymers can be manufactured with various cationic conductivities. They also exhibit excellent thermal and mechanical stability and are biocompatible, thus making them suitable materials for use in the controlled electrode coating.

In one particularly preferred embodiment, the layer extending between the electrodes comprises an ion exchange material, optionally an inert filler, and a mesoporous material. In this respect, references to a mesoporous material are to a material having pores in the range of from 1 to 75 nm, more particularly in the range of from 2 to 50 nm, as noted above. The mesoporous material provides a medium that is highly controllable and hydrates uniformly to provide a suitable medium for conduction to occur.

Suitable mesoporous materials for use in the particularly preferred sensor of the present invention, as described hereinbefore, are known in the art and commercially available, and include Zeolites. Zeolites are a particularly preferred component for inclusion in the ion exchange layer in the sensor of the present invention. One preferred zeolite is Zeolite 13X. Alternative mesoporous materials for use are Zeolite 4A or Zeolite P. The ion exchange layer may contain one or a combination of zeolite materials.

The granularity and thickness of the mesoporous material will determine the response of the sensor to changes in the composition of the gas stream in contact with the ion exchange layer. To minimize internal resistance within the sensor, it is preferred to use an ultra thin layer containing mesoporous material.

The mesoporous material is preferably dispersed in the ion exchange layer, most preferably as a fine dispersion. The mesoporous material is preferably dispersed as particles having a particle size in the range of from 0.5 to 20 μm, more preferably from 1 to 10 μm. The particles of mesoporous material are preferably finely dispersed in the ion exchange layer such that adjacent particles are generally at least one particle diameter apart, more preferably generally from at least 3 to 5 particles diameters apart. More highly dispersed arrangements may also be used, with particles up to 10 diameters apart, for example, if required.

The sensor comprising a layer of ion-exchange material with a sparse population of mesoporous material therein may be prepared using any suitable technique. In one preferred method, the ion-exchange/mesoporous material layer is applied in a two-stage process. In the method, the particles of mesoporous material are applied first, for example by contacting the sensor to be coated with a suspension of mesporous particles of the desired dispersion in a suitable solvent, such as an alcohol. The solvent is removed, for example by evaporation, leaving a layer of dispersed mesoporous particles. Other techniques to deposit the particulate mesoporous material onto the surface of the sensors may also be used. Examples of other techniques include: dry aerosol deposition, spray pyrolysis, and screen printing. More complex techniques may also be employed, such as: in-situ crystal growth, hydrothermal growth, sputtering, autoclaving, and the like.

Thereafter, a layer of ion-exchange material may be applied to the required thickness. This may be accomplished by dispensing the required volume of ion-exchange material in a suitable solvent onto the layer of dispersed mesoporous material. The solvent is then allowed to evaporate, leaving the required layer of ion-exchange material containing the mesoporous particles retained therein in a highly dispersed arrangement.

In summary, in one embodiment, the mesoporous material is applied to the electrodes as a suspension of particles in a suitable solvent, with the solvent being allowed to evaporate to leave a fine dispersion of particles over the electrodes. Ion exchange material is then applied over the mesoporous dispersion. The mesoporous material is preferably applied in a concentration of from 0.01 to 1.0 g, as a uniform suspension in 10 ml of solvent, into which the electrode assembly is dipped one or more times. More preferably, the mesporous material is applied in a concentration of from 0.05 to 0.5 g per 10 ml of solvent, especially about 0.1 g per 10 ml of solvent. Suitable solvents for use in the application of the mesoporous material are known in the art and include alcohols, in particular methanol, ethanol and higher aliphatic alcohols. The dispersion of the mesoporous particles on the sensor element may be controlled by varying the concentration of the suspension of the particles and by the number and nature of contacts between the suspension and the sensor element.

It has been found that the sparse population of mesoporous particles within the (continuous) ion exchange film affords the highest discrimination towards the detection of target species in the gas stream, in particular water vapour. In particular, it has been found that a sensor having a layer of ion-exchange material comprising zeolite particles dispersed therein, as described above, is particularly sensitive to changes in the concentration of water vapour in the gas stream. In this way, the sensor may be used with a very high specificity to the detection of water vapour and a measurement of the water vapour concentration. Examination under a scanning electron microscope (SEM) of a preferred arrangement reveals a density of mesoporous particles such that each particle is, on average, distanced several body diameters, in particular from 1 to 5 body diameters, more preferably from 1 to 3 body diameters, away from the nearest neighbour.

It has also been found that thick films of ion exchange material degrade the performance of the sensor, as do thick continuous coats of the mesoporous material. In other words, it is the combination of a thin ion exchange layer and sparse population of mesoporous particles that performs best.

A further sensor embodiment comprises a solid electrolyte precursor extending between and in contact with the working electrode and the counter electrode; whereby the gas stream may be caused to impinge upon the solid electrolyte precursor such that the water vapour in the gas stream at least partially hydrates the precursor to form an electrolyte in electrical contact with the working electrode and the counter electrode.

In the context of the present invention, the term 'solid electrolyte precursor' is a reference to a material that is in the solid phase under the conditions prevailing during the use of the sensor and that can react with (or be hydrated by) water vapour in the gas stream to reconstitute a hydrous electrolyte, allowing current to flow between the working electrode and counter electrode.

The solid electrolyte precursor comprises a ligand, preferably an organic ligand (hereafter denoted as 'L'), which is capable of forming a complex with a metal ion (hereafter denoted as 'M') to form an organometallic complex. Within the electrolyte, the organic ligand is capable of dissociation according to the following equations:

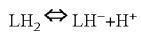

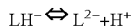

A wide range of ligands and metal ions may be employed in the organometallic complex of the solid electrolyte precursor. Preferred organic compounds for use as the ligand are amines, in particular diamines, such as diaminopropane, and carboxylic acids, especially dicarboxylic acids. The metal ions are preferably ions of Group VIII of the Periodic Table of the Elements (as provided in the Handbook of Chemistry and Physics, $62^{nd}$ edition, 1981 to 1982, Chemical Rubber Company). Suitable metals include copper, lead and cadmium.

The solid electrolyte precursor preferably also comprises a salt. Metal halide salts are preferred, in particular sodium and potassium halides, especially chlorides.

The specific choice and combination of metal ions and organic ligands may be theoretically calculated using principles of equilibrium (speciation) chemistry. The principle determinand is that the ligand should have a low $pK_b$. As noted above, a preferred class of ligand is the diamines, for example, propanediamine, ethylenediamine and various substituted diamines. The performance of the sensor is dependant on the choice and concentration of metal/ligand pairs and the optimum precursor composition may be found by routine experimentation.

A particularly preferred composition for the solid electrolyte precursor comprises copper, propanediamine and potassium chloride. One preferred composition has these components present in the following amounts: 4 mM copper, 10 mM propanediamine, and 0.1M potassium chloride as base electrolyte.

It will be appreciated by those skilled in the art that there are a considerable range and combination of other metals, ligands, and base electrolytes.

The solid electrolyte precursor may be prepared from a solution of the constituent components in a suitable solvent. Water is a most convenient solvent. The solvent is removed by drying and evaporation, to leave the solid electrolyte precursor. Evaporation of the solvent may be assisted by blowing a gas stream, such as air or nitrogen, across the surface of the drying precursor.

The present invention provides a sensor that is particularly compact and of very simple construction. In addition, the sensor may be used at ambient temperature conditions, without the need for any heating or cooling, while at the same time producing an accurate measurement of the target substance concentration in the gas being analysed.

The sensor preferably comprises a housing or other protective body to enclose and protect the electrodes. The sensor may comprise a passage or conduit to direct the stream of gas directly onto the electrodes. In a very simple arrangement, the sensor comprises a conduit or tube into which the two electrodes extend, so as to be contacted directly by the gaseous stream passing through the conduit or tube. When the sensor is intended for use in the analysis of the breath of a patient, the conduit may comprise a mouthpiece, into which the patient may exhale. Alternatively, the sensor may be formed to have the electrodes in an exposed position on or in the housing, for direct measurement of a bulk gas stream. The precise form of the housing, passage or conduit is not critical to the operation or performance of the sensor and may take any desired form. It is preferred that the body or housing of the sensor is prepared from a non-conductive material, such as a suitable plastic.

The electrodes may have any suitable shape and configuration. Suitable forms of electrode include points, lines, rings and flat planar surfaces. The effectiveness of the sensor can depend upon the particular arrangement of the electrodes and may be enhanced in certain embodiments by having a very small path length between the adjacent electrodes. This may be achieved, for example, by having each of the working and counter electrodes comprise a plurality of electrode portions arranged in an alternating, interlocking pattern, that is in the form of an array of interdigitated electrode portions, in particular arranged in a concentric pattern.

The electrodes are preferably oriented as close as possible to each other, to within the resolution of the manufacturing technology. The working and counter electrode can be between 10 to 1000 microns in width, preferably from 50 to 500 microns. The gap between the working and counter electrodes can be between 20 and 1000 microns, more preferably from 50 to 500 microns. The optimum track-gap distances are found by routine experiment for the particular electrode material, geometry, configuration, and substrate under consideration. In a preferred embodiment the optimum working electrode track widths are from 50 to 250 microns, preferably about 100 microns, and the counter electrode track widths are from 50 to 750 microns, preferably about 500 microns. The gaps between the working and counter electrodes are preferably about 100 microns.

The counter electrode and working electrode may be of equal size. However, in one preferred embodiment, the surface area of the counter electrode is greater than that of the working electrode to avoid restriction of the current transfer. Preferably, the counter electrode has a surface area at least twice that of the working electrode. Higher ratios of the surface area of the counter electrode and working electrode, such as at least 3:1, preferably at least 5:1 and up to 10:1 may also be employed. The thickness of the electrodes is determined by the manufacturing technology, but has no direct influence on the electrochemistry. The magnitude of the resultant electrochemical signal is determined principally by exposed surface area, that is the surface area of the electrodes directly exposed to and in contact with the gaseous stream. Generally, an increase in the surface area of the electrodes will result in a higher signal, but may also result in increased susceptibility to noise and electrical interference. However, the signals from smaller electrodes may be more difficult to detect.

The electrodes may be supported on a substrate. Suitable materials for the support substrate are any inert, non-conducting material, for example ceramic, plastic, or glass. The substrate provides support for the electrodes and serves to keep them in their proper orientation. Accordingly, the substrate may be any suitable supporting medium. It is important that the substrate is non-conducting, that is electrically insulating or of a sufficiently high dielectric coefficient.

The electrodes may be disposed on the surface of the substrate, with the layer of ion exchange material extending over the electrodes and substrate surface. Alternatively, the ion exchange material may be applied directly to the substrate, with the electrodes being disposed on the surface of the ion exchange layer. This would have the advantage of providing mechanical strength and a thin layer of base giving greater control of path length.

The ion exchange material is conveniently applied to the surface of the substrate by evaporation from a suspension or solution in a suitable solvent. For example, in the case of sulphonated tetrafluoroethylene copolymers, a suitable solvent is methanol. The suspension or solution of the ion exchange material may also comprise the inert support or a precursor thereof, if one is to be present in the ion exchange layer.

To improve the electrical insulation of the electrodes, the portions of the electrodes that are not disposed to be in contact with the gaseous stream (that is the non-operational portions of the electrodes) may be coated with a dielectric material, patterned in such a way as to leave exposed the active portions of the electrodes.

While the sensor operates well with two electrodes, as hereinbefore described, arrangements with more than two electrodes, for example including a third or reference electrode, as is well known in the art. The use of a reference electrode provides for better potentiostatic control of the applied voltage, or the galvanostatic control of current, when the "iR drop" between the counter and working electrodes is substantial. Dual 2-electrode and 3-electrode cells may also be employed.

A further electrode, disposed between the counter and working electrodes, may also be employed. The temperature of the gas stream may be calculated by measuring the end-to-end resistance of the electrode. Such techniques are known in the art.

The electrodes may comprise any suitable metal or alloy of metals, with the proviso that the electrode does not react with the electrolyte or any of the substances present in the gas stream. Preference is given to metals in Group VIII of the Periodic Table of the Elements (as provided in the Handbook of Chemistry and Physics, $62^{nd}$ edition, 1981 to 1982, Chemical Rubber Company). Preferred Group VIII metals are rhenium, palladium and platinum. Other suitable metals include silver and gold. Preferably, each electrode is prepared from gold or platinum. Carbon or carbon-containing materials may also be used to form the electrodes.

The electrodes of the sensor of the present invention may be formed by printing the electrode material in the form of a thick film screen printing ink onto the substrate. The ink consists of four components, namely the functional component, a binder, a vehicle and one or more modifiers. In the case of the present invention, the functional component forms the conductive component of the electrode and comprises a powder of one or more of the aforementioned metals used to form the electrode.

The binder holds the ink to the substrate and merges with the substrate during high temperature firing. The vehicle acts as the carrier for the powders and comprises both volatile components, such as solvents and non-volatile components, such as polymers. These materials evaporate during the early stages of drying and firing respectively. The modifiers comprise small amounts of additives, which are active in controlling the behaviour of the inks before and after processing.

Screen printing requires the ink viscosity to be controlled within limits determined by rheological properties, such as the amount of vehicle components and powders in the ink, as well as aspects of the environment, such as ambient temperature.

The printing screen may be prepared by stretching stainless steel wire mesh cloth across the screen frame, while maintaining high tension. An emulsion is then spread over the entire mesh, filling all open areas of the mesh. A common practice is to add an excess of the emulsion to the mesh. The area to be screen printed is then patterned on the screen using the desired electrode design template.

The squeegee is used to spread the ink over the screen. The shearing action of the squeegee results in a reduction in the viscosity of the ink, allowing the ink to pass through the patterned areas onto the substrate. The screen peels away as the squeegee passes. The ink viscosity recovers to its original state and results in a well-defined print. The screen mesh is critical when determining the desired thick film print thickness, and hence the thickness of the completed electrodes.

The mechanical limit to downward travel of the squeegee (downstop) should be set to allow the limit of print stroke to be 75-125 um below the substrate surface. This will allow a consistent print thickness to be achieved across the substrate whilst simultaneously protecting the screen mesh from distortion and possible plastic deformation due to excessive pressure.

To determine the print thickness the following equation can be used:

$$Tw = (Tm \times Ao) + Te$$

Where Tw=Wet thickness (um);
Tm=mesh weave thickness (um);
Ao=% open area;
Te=Emulsion thickness (um).

After the printing process the sensor element needs to be leveled before firing. The leveling permits mesh marks to fill and some of the more volatile solvents to evaporate slowly at room temperature. If all of the solvent is not removed in this drying process, the remaining amount may cause problems in the firing process by polluting the atmosphere surrounding the sensor element. Most of the solvents used in thick film technology can be completely removed in an oven at 150° C. when held there for 10 minutes.

Firing is typically accomplished in a belt furnace. Firing temperatures vary according to the ink chemistry. Most commercially available systems fire at 850° C. peak for 10 minutes. Total furnace time is 30 to 45 minutes, including the time taken to heat the furnace and cool to room temperature. Purity of the firing atmosphere is critical to successful processing. The air should be clean of particulates, hydrocarbons, halogen-containing vapours and water vapour.

Alternative techniques for preparing the electrodes and applying them to the substrate, if present, include spin/sputter coating and visible/ultraviolet/laser photolithography. In order to avoid impurities being present in the electrodes, which may alter the electrochemical performance of the sensor, the electrodes may be prepared by electrochemical plating. In particular, each electrode may be comprised of a plurality of layers applied by different techniques, with the lower layers be prepared using one of the aforementioned techniques, such as printing, and the uppermost or outer layer or layers being applied by electrochemical plating using a pure electrode material, such as a pure metal.

In use, the sensor is able to operate over a wide range of temperatures.

In a further aspect, the present invention provides a method of determining the carbon dioxide content of an exhaled gas stream comprising water vapour, the method comprising:

causing the gas stream to impinge on a sensing element comprising a working electrode and a counter electrode;

applying an electric potential across the working electrode and counter electrode;

measuring the current flowing between the working electrode and counter electrode as a result of the applied potential;

determining from the measured current flow an indication of the concentration of water vapour in the gas stream; and determining the concentration of carbon dioxide in the exhaled gas stream from the measured water vapour concentration.

During operation, the impedance between the counter and working electrodes indicates the relative humidity and, if being measured, the target substance content of the gaseous stream, which may be electronically measured by a variety of techniques.

The method of the present invention may be carried out using a sensor as hereinbefore described.

The method requires that an electric potential is applied across the electrodes. In one simple configuration, a voltage is applied to the counter electrode, while the working electrode is connected to earth (grounded). In its simplest form, the method applies a single, constant potential difference across the working and counter electrodes. Alternatively, the potential difference may be varied against time, for example being pulsed or swept between a series of potentials. In one embodiment, the electric potential is pulsed between a so-called 'rest' potential, at which no reaction occurs, and a reaction potential.

In operation, a linear potential scan, multiple voltage steps or one discrete potential pulse are applied to the working electrode, and the resultant Faradaic reduction current is monitored as a direct function of the dissolution of target molecules in the water bridging the electrodes.

The measured current in the sensor element is usually small. The current is converted to a voltage using a resistor, R. As a result of the small current flow, careful attention to electronic design and detail may be necessary. In particular, special "guarding" techniques may be employed. Ground loops need to be avoided in the system. This can be achieved using techniques known in the art.

The current that passes between the counter and working electrodes is converted to a voltage and recorded as a function of the carbon dioxide concentration in the gaseous stream. The sensor responds faster by pulsing the potential between two voltages, a technique known in the art as 'Square Wave Voltammetry'. Measuring the response several times during a pulse may be used to assess the impedance of the sensor.

The shape of the transient response can be simply related to the electrical characteristics (impedance) of the sensor in terms of simple electronic resistance and capacitance elements. By careful analysis of the shape, the individual contributions of resistance and capacitance may be calculated. Such mathematical techniques are well known in the art. Capacitance is an unwanted noisy component resulting from electronic artifacts, such as charging, etc. The capacitive signal can be reduced by selection of the design and layout of the electrodes in the sensor. Increasing the surface area of the electrodes and increasing the distance between the electrodes are two major parameters that affect the resultant capacitance. The desired Faradaic signal resulting from the passage of current due to reaction between the electrodes may be optimized, by experiment. Measurement of the response at increasing periods within the pulse is one technique that can preferentially select between the capacitive and Faradaic components, for instance. Such practical techniques are well known in the art.

The potential difference applied to the electrodes of the sensor element may be alternately or be periodically pulsed between a rest potential and a reaction potential, as noted above. FIG. 1 shows examples of voltage waveforms that may be applied. FIG. 1a is a representation of a pulsed voltage signal, alternating between a rest potential, $V_O$, and a reaction potential $V_R$. The voltage may be pulsed at a range of frequencies, typically from sub-Hertz frequencies, that is from 0.1 Hz, up to 10 kHz. A preferred pulse frequency is in the range of from 1 to 500 Hz. Alternatively, the potential waveform applied to the counter electrode may consist of a "swept" series of frequencies, represented in FIG. 1b. A further alternative waveform shown in FIG. 1c is a so-called "white noise" set of frequencies. The complex frequency response obtained from such a waveform will have to be deconvoluted after signal acquisition using techniques such as Fourier Transform analysis. Again, such techniques are known in the art.

One preferred voltage regime is 0V ("rest" potential), 250 mV ("reaction" potential), and 20 Hz pulse frequency.

It is an advantage of the present invention that the electrochemical reaction potential is approximately +0.2 volts, which avoids many if not all of the possible competing reactions that would interfere with the measurements, such as the reduction of metal ions and the dissolution of oxygen.

The method of the present invention is particularly suitable for use in the analysis of the exhaled breath of a person or animal. From the results of this analysis, an indication of the respiratory condition of the patient may be obtained.

The sensor and method of the present invention are of use in monitoring and determining the lung function of a patient or subject. The method and sensor are particularly suitable for analyzing tidal concentrations of carbon dioxide in the exhaled breath of a person or animal, to diagnose or monitor a variety of respiratory conditions. The sensor is particularly useful for applications requiring fast response times, for example personal respiratory monitoring of tidal breathing (capnography). Capnographic measurements can be applied generally in the field of respiratory medicine, airway diseases, both restrictive and obstructive, airway tract disease management, and airway inflammation. The present invention finds particular application in the field of capnography and asthma diagnosis, monitoring and management, where the shape of the capnogram changes as a function of the extent of the disease. In particular, due to the high rate of response that may be achieved using the sensor and method of the present invention, the results may be used to provide an early alert to the onset of an asthma attack in an asthmatic patient.

As noted above, it has been found that the concentration of carbon dioxide and water vapour in the gas stream exhaled by a subject are closely related, such that changes in the carbon dioxide concentration can be monitored by measuring changes in the concentration of water vapour. As discussed above, a knowledge of the carbon dioxide concentration in the breath exhaled by a subject can provide very valuable information about the health of the subject, in particular the condition and performance of the lungs in particular and respiratory system in general. However, it has further been found that the condition and performance of the respiratory system of a subject in general, and the lungs of the subject in particular, can be readily determined directly from measurement and monitoring of the water vapour content of the gas stream exhaled by the subject.

Accordingly, in a further aspect, the present invention provides a method of determining the respiratory function of a subject, the method comprising:

measuring the concentration of water vapour in the gas stream exhaled by the subject; and from the measured water vapour concentration determining the respiratory function of the subject.

The method may be used to provide a determination of the function of the overall respiratory system of the subject, but is particularly suitable for determining the function of the lungs of the subject.

The measurement of the water vapour content of the exhaled gas stream may be applied to gas exhaled through either the nose and/or the mouth of the subject. In a preferred embodiment, the measurement is made of the water vapour content of the gas stream exhaled through the mouth of the subject.

In addition, water vapour present in the gas stream exhaled by a subject is produced by metabolic processes occurring within the body of the subject. Accordingly, the measurement of the water vapour content of the exhaled gas stream can be used to provide a direct indication of the nature and performance of a number of metabolic processes of the subject, and/or provide an overall indication of the metabolism of the subject. This can in turn be used to derive important information relating to the general condition of the subject, as well as information relating to specific conditions of illnesses being experienced by the subject.

As with the concentration of carbon dioxide in the exhaled gas stream of a subject, the concentration of the water vapour in the exhaled breath changes throughout the duration of the breath. In particular, a graphical trace of the water vapour concentration can be obtained, which is similar in overall form to a capnogram obtained from the measurement of carbon dioxide concentration in the exhaled gas stream. The graphical trace of the water vapour concentration obtained can be subjected to an analysis similar to that known for capnograms. Specific techniques for the analysis of the water vapour traces, as well as capnograms, are described hereinafter and form another aspect of the present invention.

The measurement of the water vapour content of the exhaled breath may be carried out for a portion of the duration of an exhalation or, more preferably, over the entire duration of an exhaled breath. More preferably, the changes in the water vapour concentration are measured over several cycles of inhalation and exhalation, that is the measurement of the water vapour concentration is obtained for tidal breathing.

Any suitable device may be used to measure the concentration of water vapour in the exhaled gas stream of the subject. The device is preferably an electrochemical sensor, which has been found to be particularly convenient for use in measuring the concentration of water vapour. A particularly preferred form of electrochemical sensor is described in general terms hereinbefore and in detail hereinafter.

As noted, the concentrations of gaseous species in the exhaled breath of a subject may be measured and their variations over the time of the exhalation determined. The measurements thus obtained may be presented graphically in the form of a trace, known in the case of carbon dioxide as a capnogram. The trace for carbon dioxide and water vapour are similar and have a generally rectangular form, with the concentrations rising steeply in the initial period of the exhalation, reaching a generally flat or plateau region, and then falling in the final stages of the exhaled breath. A typical trace is shown in FIG. 10, where variations in the concentration of carbon dioxide in the exhaled gas stream over time are plotted for a single exhaled breath.

Monitoring the change in concentration of components in an expired gas stream of a subject, in particular during normal tidal breathing, is non-invasive and generally easy to carry out. In particular, the subject is not required to exert any additional effort when exhaling, as is the case with other techniques. The trace of changes in concentration over time of expiration reflects both volumetric changes and physiological changes in the lungs of the subject. Analysis of the shape of the trace can provide valuable information and indications of general lung function and of a wide range of conditions and afflictions of the lungs. The present invention provides two specific methods for analyzing the trace of concentration versus time for components of the exhaled gas stream of a subject.

Referring to FIG. 10, the trace of concentration of gaseous components in the expired gas stream with time is shown and discussed in detail in the specific examples below. However, in general terms, the trace can be seen to comprise an ascending phase, with the concentration increasing rapidly with time as subject breathes out. There follows a plateau phase, with the concentration changing significantly less than the ascending phase. Finally, towards the end of the breath, the concentration falls rapidly in a descending phase. The ascending phase and plateau phase are particularly affected by changes in ventilation (V) and perfusion (Q) of the subject. In a first specific method, the slope of the ascending phase and/or the plateau phase are used to determine lung function.

Accordingly, there is further provided by the present invention a method of determining the lung function of a subject, the method comprising:

measuring the change in concentration of a gaseous component of the exhaled gas stream of the subject;

determining the change in concentration as a function of time for the exhaled gas stream to obtain a profile of the change in concentration with time;

measuring the slope of the ascending phase of the profile; and using the slope of the ascending phase making a determination of the lung function of the subject.

The angle of the ascending phase to the x-axis or the slope of the ascending phase changes with variations in the lung function and condition. This allows the angle or slope of the ascending phase to be measured and a determination made of the lung function of the subject. An indication of lung function for the subject may be obtained, for example, by comparing the angle of the ascending phase in a given trace to the angle of the corresponding phase in other traces obtained for the same subject. In this way, changes in the lung function of the subject over time may be monitored, for example to provide an early indication of the onset of a particular condition, for example asthma, COPD, and the like.

Further, the changes or trends in the trace obtained from measurements of the water vapour content of the exhaled gas streams of a subject are particularly useful once a particular condition has been identified or diagnosed. In particular, the method and apparatus of the present invention allow the changes in the condition of the subject to be monitored by identifying changes and trends in the trace over a period of time. In this way, for example, the response of the subject to a particular treatment may be gauged and appropriate action taken if the condition is worsening or not improving as expected.

The method may solely measure the slope of the ascending phase and use this in the determination of lung function. However, the method may also employ the slope of the plateau phase of the trace of concentration with time. During this phase, while the concentration of the gaseous component does not generally change as significantly as in the ascending phase, the concentration will vary over time between the end of the ascending phase and the beginning of the descending phase. As noted above, the angle or slope of the plateau phase can also be affected by changes in lung function of the subject. Thus, the determination of lung function may also make use of the angle or slope of the plateau phase of the trace. In particular, the ratio of the slopes of the ascending phase and the plateau phase may be calculated. It has been found that this ratio can also be used to provide an indication of lung function, in particular changes in the ratio indicating the potential onset of certain conditions in the lungs, such as asthma, COPD and the like.

The method may be carried out by measuring one or more of the gaseous components of the exhaled gas stream, most preferably using carbon dioxide or water vapour.

In addition, or as an alternative, to the use of the slopes of the trace, it has also been found that the region of the trace surrounding the transition from the ascending phase to the plateau phase can provide very valuable indications regarding lung function of the subject.

Accordingly, in a further aspect, the present invention provides a method of determining the lung function of a subject, the method comprising:

measuring the change in concentration of a gaseous component of the exhaled gas stream of the subject;

determining the change in concentration as a function of time for the exhaled gas stream to obtain a profile of the change in concentration with time;

analyzing the portion of the profile in the region of the transition from the ascending phase to the plateau phase; and using the results of the analysis to make a determination of the lung function of the subject.

The method employs an analysis of the region of the concentration—time trace surrounding the transition between the ascending phase and the plateau phase. Suitable analysis techniques are mathematical transformations, including regression techniques to calculate a line of best fit through the transformed data. The coefficient of the best fit provides an indication of lung function, in particular the level of breathlessness that the subject is experiencing. The best fit may be calculated using any suitable mathematical technique, for example least squares, median fit, and the like. Other techniques for transforming the data may also be employed, and include polynomial, spline and the like.

Any range of data points from the trace may be used, provided they span the transition from the ascending phase to the plateau phase. It is preferred to use data from at least the mid point of the ascending phase and the end of the plateau phase.

Again, the method may employ measurement of one or more gaseous components of the exhaled gas stream, most preferably carbon dioxide or water vapour.

A specific example of the method of analysis is given in the examples hereinafter.

As noted above, one technique for monitoring the condition of the respiratory system of a subject, in particular lung function, is to measure the changes in concentration of a gaseous component of the gas stream exhaled by the subject and determine the trace or curve of concentration against time. The shape of the trace will vary as the lung function of the subject changes, for example a given condition begins, worsens or improves. This, in turn provides a technique for monitoring the lung function of the subject.

Accordingly, the present invention also provides a method for monitoring the lung function of a subject, the method comprising the steps of:

measuring the change in concentration of a gaseous component of the exhaled gas stream of the subject;

determining the change in concentration as a function of time for the exhaled gas stream to obtain a profile of the change in concentration with time;

comparing the profile thus obtained with a pre-existing profile; and using the comparison in making a determination of the lung function of the subject.

There is also provided a device for monitoring the lung function of a subject, the method comprising the steps of:

means for measuring the change in concentration of a gaseous component of the exhaled gas stream of the subject;

means for determining the change in concentration as a function of time for the exhaled gas stream to obtain a profile of the change in concentration with time;

means for storing a plurality of profiles; and means for comparing the profile thus obtained with a pre-existing profile retrieved from the storage means.

The profile obtained from an analysis of the concentration of a gaseous component of the exhaled gas stream is compared with a pre-existing profile. The pre-existing profile may be that of, or representative of, a healthy subject. In this way, an indication of the lung function of the subject may be obtained by direct comparison with the normal or healthy profile. Alternatively, as noted, the pre-existing profile may be one obtained from the same subject at an earlier time. In this way, the progress or development of the subject may be monitored, for example to provide an indication of the onset, deterioration or improvement of a particular condition, such as asthma or COPD or the like.

The method may use one pre-existing profile or trace. Alternatively, a plurality of pre-existing profiles may be used, for example to provide a pattern of lung function over an extended period of time. In such a case, the means for storing the profiles may store a library of pre-existing profiles.

The comparison of the profiles may be as simple as providing a display where images of two or more profiles are displayed. Alternatively, the comparison may employ one or more techniques for analyzing the trace data, for example the specific techniques described hereinbefore.

Again, the method and device may be used in respect of one or more gaseous components of the exhaled gas stream, most preferably carbon dioxide or water vapour.

Embodiments of the present invention will now be described, by way of example only, having reference to the accompanying drawings, in which.

Figure 1:
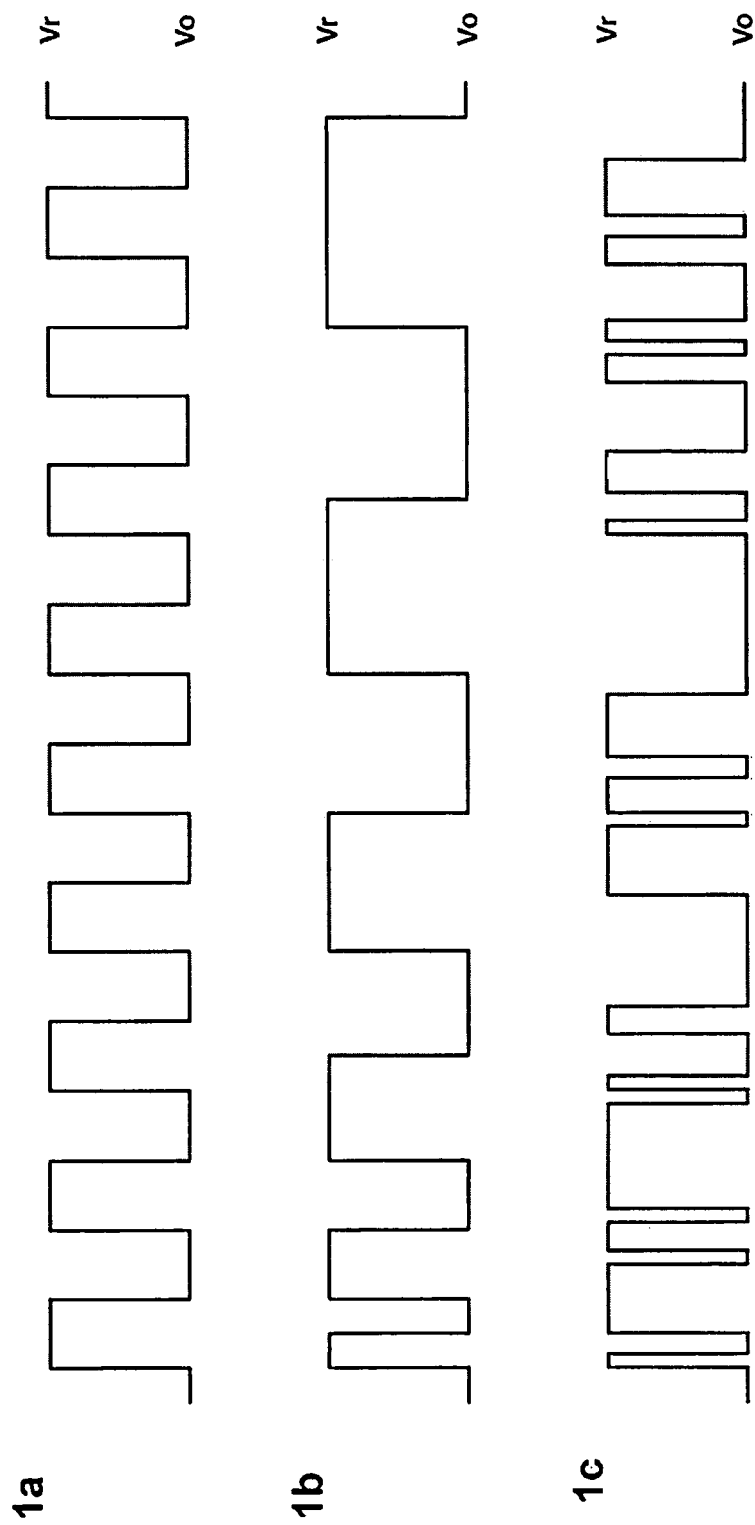
FIGS. 1a, 1b and 1c are voltage versus time representations of possible voltage waveforms that may be applied to the electrodes in the method of the present invention, as discussed hereinbefore.
Figure 2:
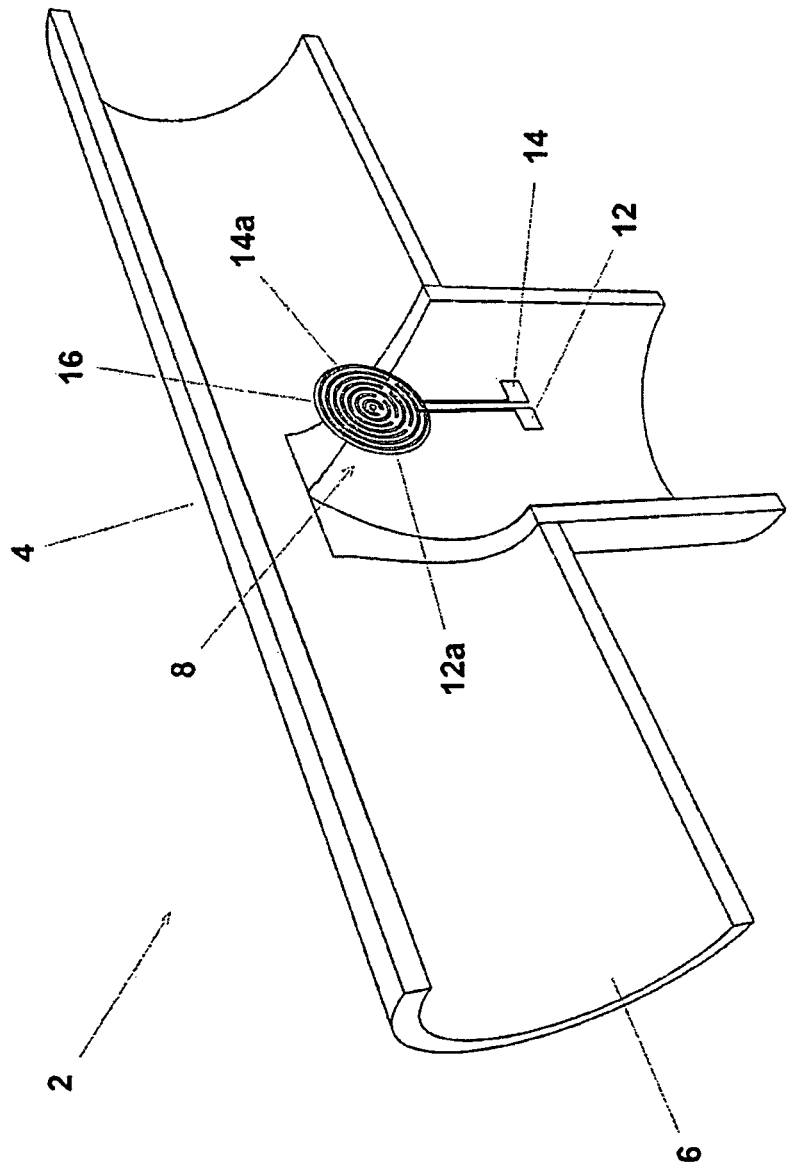
FIG. 2 is a cross-sectional representation of one embodiment of the sensor of the present invention.

Referring to FIG. 2, there is shown a sensor according to the present invention. The sensor is for analyzing the carbon dioxide content and humidity of exhaled breath. The sensor, generally indicated as 2, comprises a conduit 4, through which a stream of exhaled breath may be passed. The conduit 4 comprises a mouthpiece 6, into which the patient may breathe.

A sensing element, generally indicated as 8, is located within the conduit 4, such that a stream of gas passing through the conduit from the mouthpiece 6 is caused to impinge upon the sensing element 8. The sensing element 8 comprises a support substrate 10 of an inert material, onto which is mounted a working electrode 12 and a reference electrode 14. The working electrode 12 and reference electrode 14 each comprise a plurality of electrode portions, 12a and 14a, arranged in concentric circles, so as to provide an interwoven pattern minimizing the distance between adjacent portions of the working electrode 12 and reference electrode 14. In this way, the current path between the two electrodes is kept to a minimum.

A layer 16 of insulating or dielectric material extends over a portion of both the working and counter electrodes 12 and 14, leaving the portions 12a and 14a of each electrode exposed to be in contact with a stream of gas passing through the conduit 4. The arrangement of the support, electrodes 12 and 14, and the coating applied to the electrodes is shown in more detail in FIGS. 3 and 4.

Figure 3:
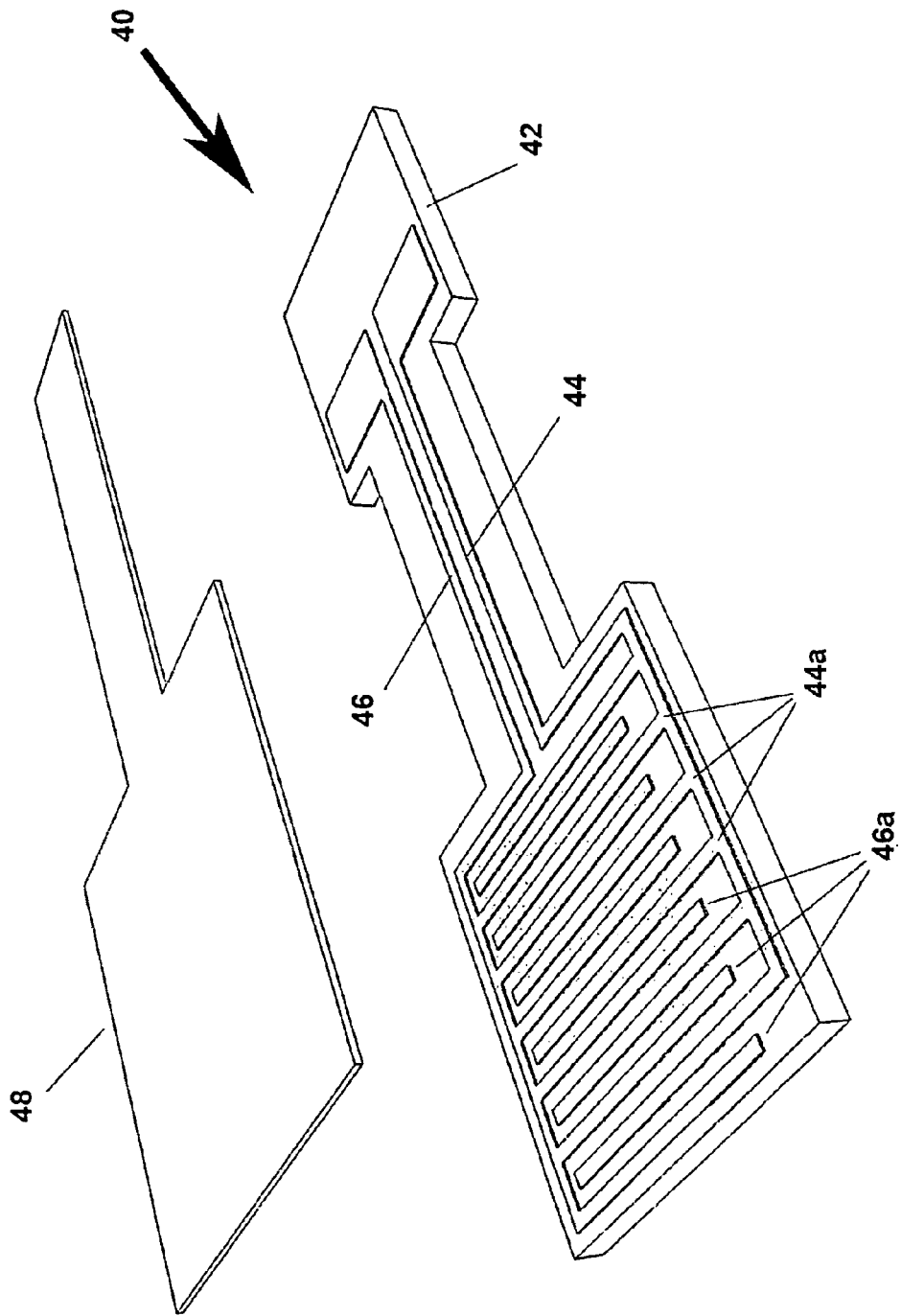
FIG. 3 is an isometric schematic view of a face of one embodiment of the sensor element according to the present invention.

Referring to FIG. 3, there is shown an exploded view of a sensor element, generally indicated as 40, comprising a substrate layer 42. A working electrode 44 is mounted on the substrate layer 42 from which extend a series of elongated electrode portions 44a. Similarly, a reference electrode 46 is mounted on the substrate layer 42 from which extends a series of electrode portions 46a. As will be seen in FIG. 3, the working electrode portions 44a and the reference electrode portions 46a extend one between the other in an intimate, interdigitated array, providing a large surface area of exposed electrode with minimum separation between adjacent portions of the working and reference electrodes. A layer 48 of coating material, for example an ion exchange material, electrolyte precursor, zeolite or mesoporous clay, overlies the working and reference electrodes 44, 46.

The coating material 48 is applied by the repeated immersion in a suspension or slurry of the coating material in a suitable solvent. The sensor element is dried to evaporate the solvent after each immersion and before the subsequent immersion. Other materials may be incorporated into the coating by subsequent immersion in additional solutions or suspensions. The number of immersions is determined by the required thickness of the coating, and the chemical composition is determined by the number and variety of additional solutions that the sensor is dipped into.

It will be obvious that there are a number of other means whereby the thickness and composition of the coating may be similarly achieved, such as: pad, spray, screen and other mechanical methods of printing. Such techniques are well known in the field.

Figure 4:
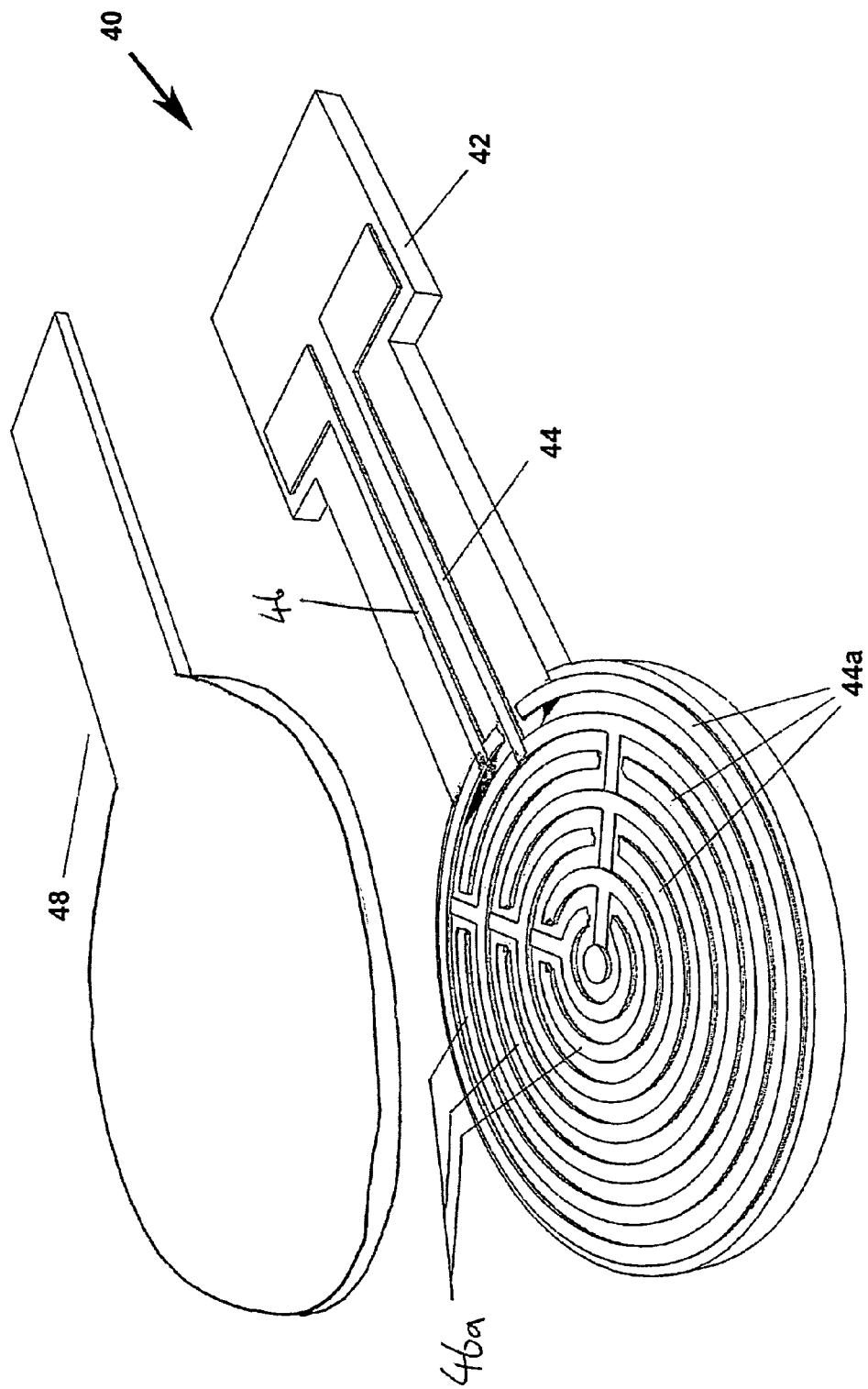
FIG. 4 is an isometric schematic view of an alternative embodiment of the sensor element of the sensor of the present invention.

An alternative electrode arrangement is shown in FIG. 4, in which components common to the sensor element of FIG. 3 are identified with the same reference numerals. It will be noted that the working electrode portions 44a and the reference electrode portions 46a are arranged in an intimate circular array. The electrodes and substrate are coated as described above in relation to FIG. 3.

Figure 13:
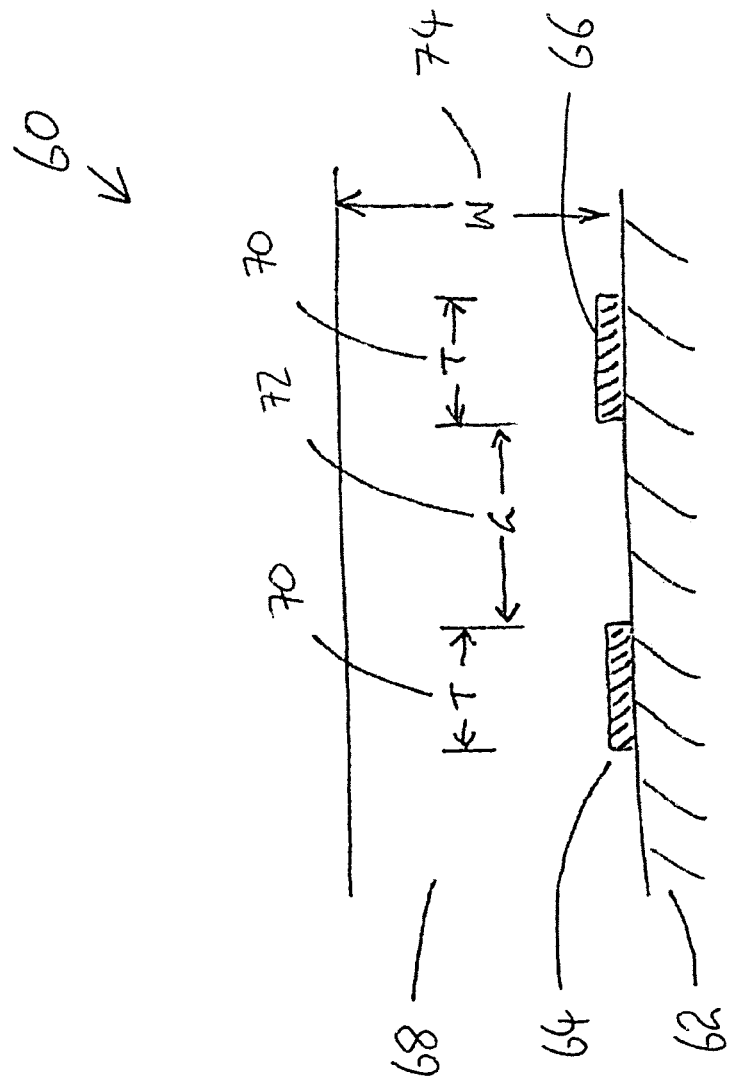
FIG. 13 is a schematic cross-sectional view through a portion of a sensor element according to a preferred embodiment of the present invention.

An enlarged cross-sectional view through a portion of a sensor element of a particularly preferred embodiment is shown in FIG. 13. The sensor element, generally indicated as 60, comprises an inert substrate 62 on which have been deposited working and counter electrodes 64 and 66, for example using the screen printing techniques hereinbefore described. A layer of ion-exchange material 68 extends over the surface of the inert substrate 62 and the electrodes 64, 66. In FIG. 13, the relative dimensions of the electrodes, their spacing and the thickness of the ion-exchange layer are indicated. In particular, the electrodes having a track width (T) 70 are separated by a gap (G) 72. The thickness (W) of the layer of ion-exchange material 74 is of the same general size as the gap 72 between the electrodes.

Figure 14:
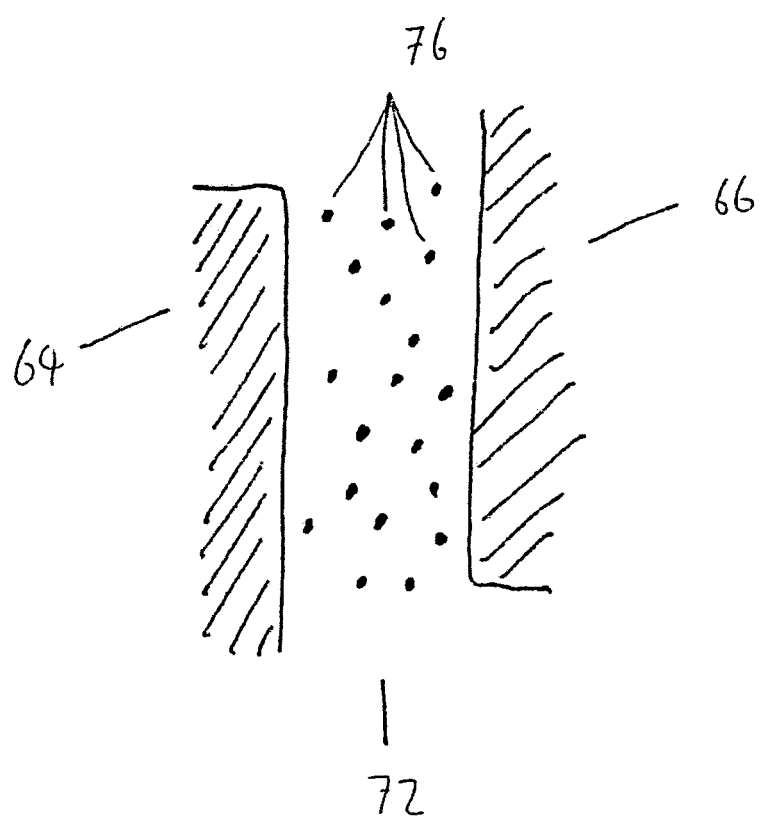
FIG. 14 is a diagrammatic representation of the distribution of mesoporous particles in a layer of ion-exchange material of the sensor of FIG. 13.
Figure 16:
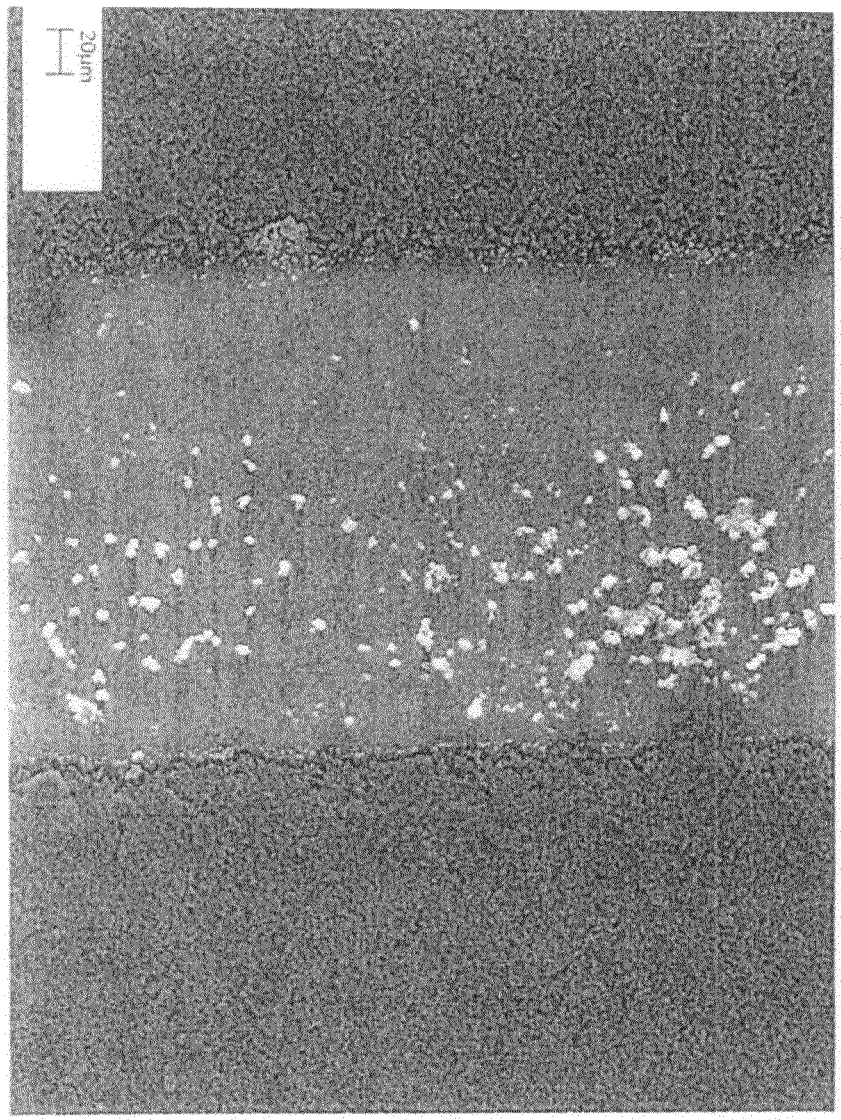
FIG. 16 is a scanning electron microscope (SEM) image of the surface of the electrodes of a sensor according to a preferred embodiment of the present invention, after deposition of particles of mesoporous material on the sensor element but before application of a layer of ion-exchange material.

Referring to FIG. 14, the general distribution of particles of mesoporous material within the ion-exchange layer 68 of the sensor element of FIG. 13 is represented in plan view. Thus, the working and counter electrodes 64, 66 are separated by the gap 72. Particles of mesoporous material 76 are shown sparsely dispersed in the layer of ion-exchange material. FIG. 14 is a diagrammatic representation of a general type of preferred sensor element, an actual example of which is shown in FIG. 16, an image taken using scanning electron microscopy (SEM) of the particles of mesoporous material dispersed on the surface of an electrode, prior to coating with a layer of ion-exchange material. The image of FIG. 16 is discussed in more detail in Example 3 below.

If the coating is considered to be as a dielectric layer limiting factor of the sensor shown in FIGS. 13 and 14 will be the relative permittivity, which is approximately 23 for Zeolite (compared to 3 for polyimide and 80 for water). Adsorption of water simultaneously increases relative permittivity, which will improve the speed of response. In other words, the speed of response increases as the thickness of the layer of ion-exchange material decreases and is fastest with thinnest coats. The layer will in many cases of thin coatings of ion-exchange material adsorb sufficient water in the first few milliseconds to facilitate measurement of the signal. Beyond the initial chemisorption, further (and continued) adsorption of water will not increase the signal significantly.

Whether the sensor impedance is resistive or capacitive, sensor response time is always limited by the rate of sorption/desorption of water from the layer of ion-exchange material and ranges from several seconds to several minutes. Thus, the substrate geometry and composition are important to optimizing sensor performance. The use of thinner coatings of ion-exchange material dramatically decreases adsorption times; the characteristic diffusion time varying as the square of the film thickness. Many prior art devices have attempted to minimize desorption times by using polymer substrates that adsorb less moisture. While this speeds response, it also decreases sensitivity. By combining the ion exchange material in an extremely thin layer with a fine dispersion of (granular) mesoporous material, in particular a Zeolite, that also increases surface area, it has been possible to achieve response times that are an order of magnitude less than those of the prior art devices.

Figure 15:
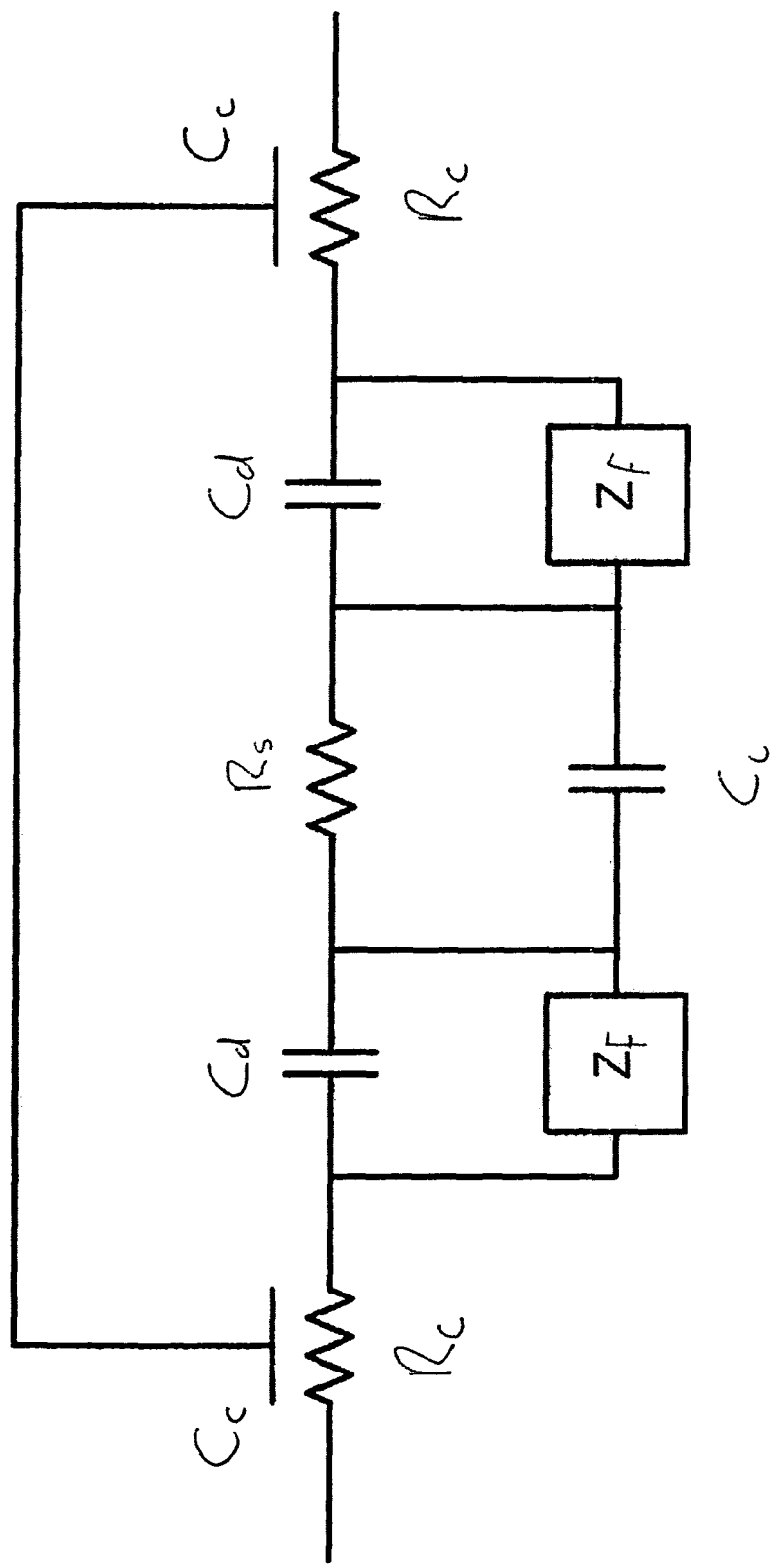
FIG. 15 is a diagrammatic representation of a notional electrical circuit representing the electrical impedances present in the sensor shown in FIGS. 13 and 14.

The track-gap distances of the electrodes and coating thickness of the ion-exchange material define the overall performance of the sensor, in particular the speed of response. In most cases, electrochemical sensors can be represented (in electrical equivalents) as a classic resistor-capacitor combination. However, the sensor of the preferred embodiment of the present invention, using a layer of ion-exchange material with finely dispersed mesoporous material, is more complicated. It is possible to interpret the sensor as a two-electrode cell, represented as a collection of resistors and capacitors. A typical representation is shown in FIG. 15. In FIG. 15, there are represented implicit connector impedances ($R_c$ and $C_c$) and each component is assumed to be symmetric (equal) at each electrode. $R_s$ is the solution resistance of the adsorbed water layer. An inter-electrode capacitance term, $C_i$, is included to account for the dielectric properties of the solute (outside the diffuse layer). Lastly, a frequency-dependent Faradaic impedance ($Z_f$), which includes both charge-transfer resistance and Warburg impedance, is included for each electrode.

Analysis of experimental impedance data obtained from a sensor as shown in FIGS. 13 and 14 shows that the sensor can be modelled in terms of resistors and capacitors. Both the resistance and capacitance of the coating changes as a function of humidity. The resistance simply limits the magnitude of the current flow through the sensor. Changing the capacitance alters the phase of the output signal (relative to the applied waveform). A high capacitance reduces speed of response, by filtering the current flowing between the electrodes. The value of the resistors and capacitors is a function of the track widths and gap distances, and of that ratio between tracks and gaps. The capacitance is principally a function of coating thickness.

Overall, as noted hereinbefore, the speed of reaction of the sensor to changes in water vapour concentration in the gas stream being monitored and the specificity of the sensor to water vapour are significantly enhanced by the use of a sensor element in which the electrodes are coated with a layer of ion-exchange material, in particular Nafion®, with a fine dispersion of particles of a mesoporous material, in particular a Zeolite, and in which the layer of the ion-exchange material with the finely distributed mesoporous particles is particularly thin.

Figure 5:
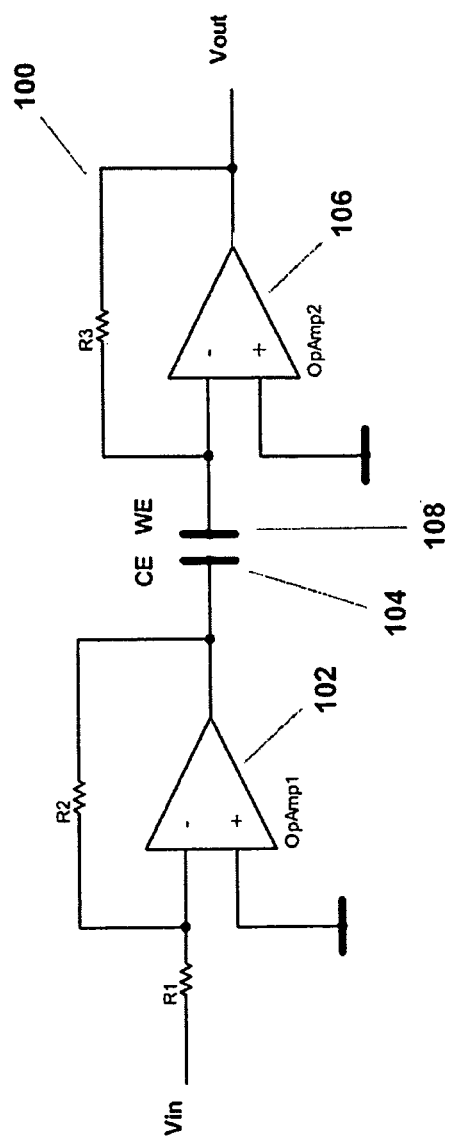
FIG. 5 is a schematic view of a potentiostat electronic circuit that may be used to excite the electrodes of the sensor element.

Referring to FIG. 5, there is shown a potentiostat electronic circuit that may be employed to provide the voltage applied across the working and reference electrodes of the sensor of the present invention. The circuit, generally indicated as 100, comprises an amplifier 102, identified as 'OpAmp1', acting as a control amplifier to accept an externally applied voltage signal $V_{in}$. The output from OpAmp1 is applied to the control (counter) electrode 104. A second amplifier 106, identified as 'OpAmp2' converts the passage of current from the counter electrode 104 to the working electrode 108 into a measurable voltage ($V_{out}$). Resistors R1, R2 and R3 are selected according to the input voltage, and measured current.

Figure 6:
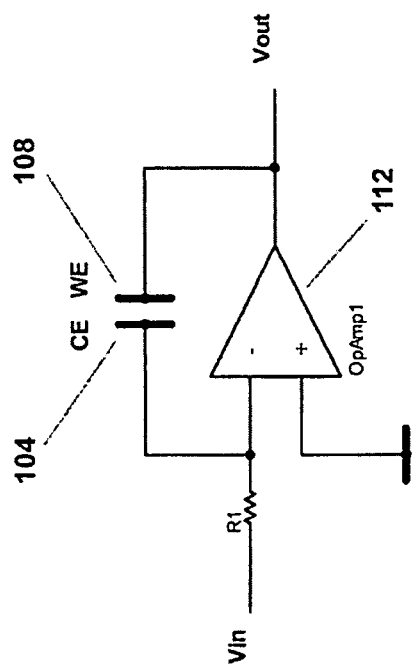
FIG. 6 is a schematic view of a galvanostat electronic circuit that may be used to excite the electrodes.

An alternative galvanostat circuit for exciting the electrodes of the sensor is shown in FIG. 6. The control and working electrodes 104 and 108 are connected between the input and output of a single amplifier 112, indicated as 'OpAmp1'. Again, resistor R1 is selected according to the desired current.

Figure 7:
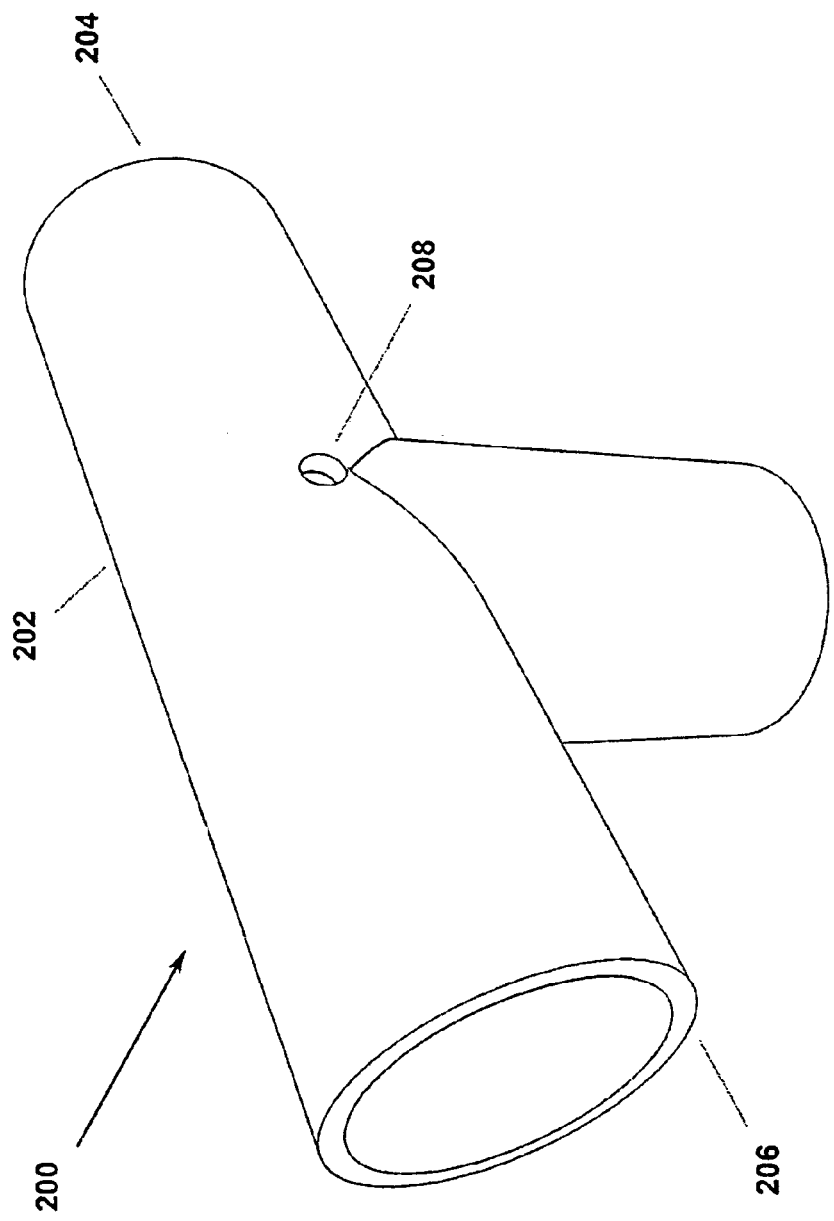
FIG. 7 is a schematic representation of a breathing tube adaptor for use in the sensor of the present invention.

Turning to FIG. 7, an adaptor for monitoring the breath of a patient is shown. A sensor element is mounted within the adaptor and oriented directly into the air stream flowing through the adaptor, in a similar manner to that shown in FIG. 2 and described hereinbefore. The preferred embodiment illustrated in FIG. 7 comprises and adaptor, generally indicated as 200, having a cylindrical housing 202 having a male-shaped (push-fit) cone coupling 204 at one end and a female-shaped (push-fit) cone coupling 206 at the other. A side inlet 208 is provided in the form of an orifice in the cylindrical housing 202, allowing for the adaptor to be used in the monitoring of the tidal breathing of a patient, as described in more detail in Example 2 below. The side inlet 208 directs gas onto the sensor element during inhalation by a patient through the device. The monitoring of tidal breathing may be improved by the provision of a one-way valve on the outlet of the housing 202.

Figure 8:
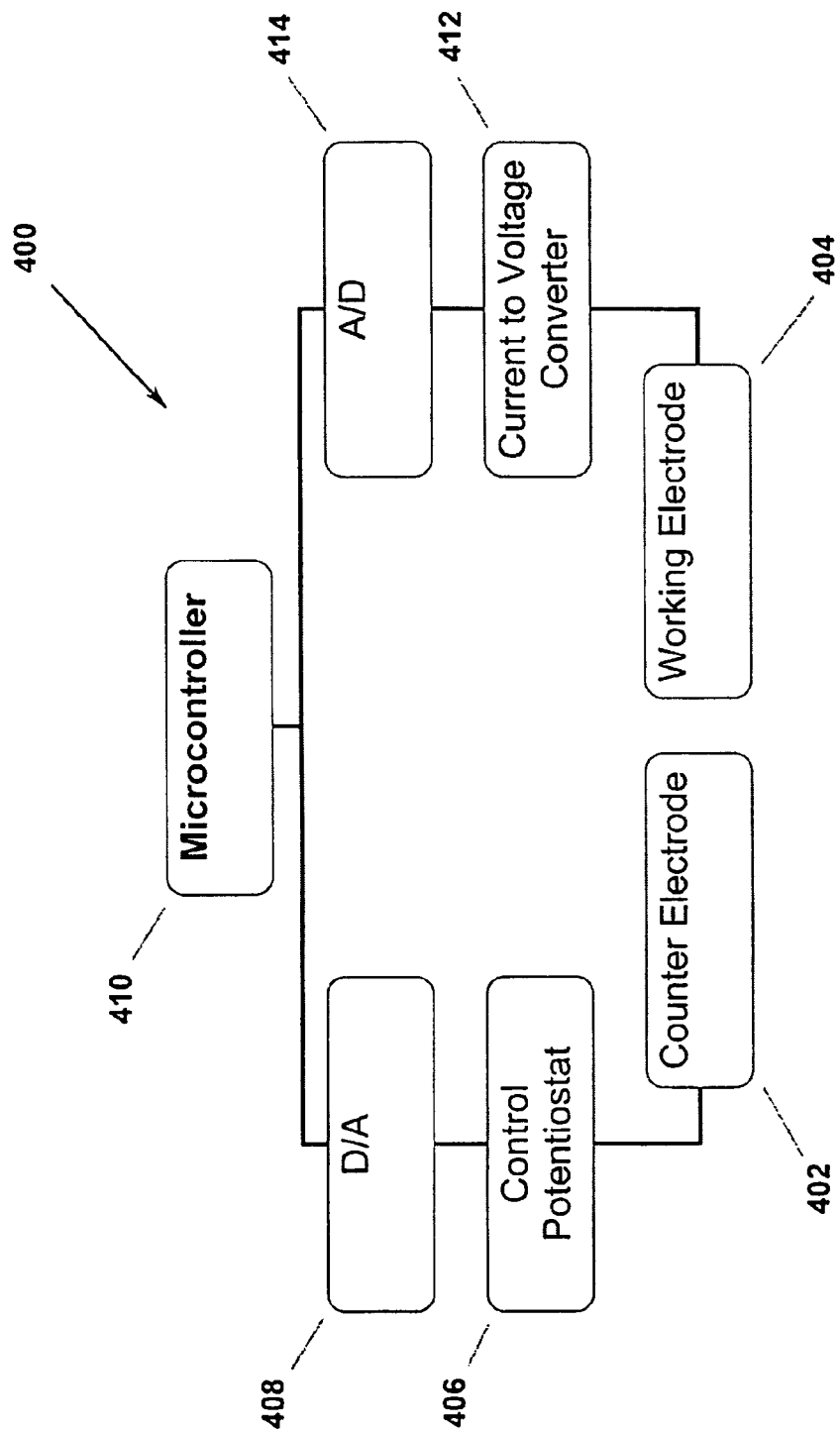
FIG. 8 is a flow-diagram providing an overview of the inter-connection of sensor elements and their connection into a suitable measuring instrument of an embodiment of the present invention.

With reference to FIG. 8 there is shown in schematic form the general layout of a sensor system according to the present invention. The system, generally indicated as 400, comprises a sensor element having a counter electrode 402 and a working electrode 404. The counter electrode 402 is supplied with a voltage by a control potentiostat 406, for example of the form shown in FIG. 5 and described hereinbefore. The input signal for the control potentiostat 406 is provided by a digital-to-analog converter (D/A) 408, itself being provided with a digital input signal from a microcontroller 410. The output signal generated by the sensing element is in the form of a current at the working electrode 404, which is fed to a current-to-voltage converter 412, the output of which is in turn fed to an analog-to-digital converter (A/D) 414. The microcontroller 410 receives the output of the A/D converter 414, which it employs to generate a display indicating the concentration of the target substance in the gas stream being monitored. The display (not shown in FIG. 8 for reasons of clarity) may be any suitable form of display, for example an audio display or visual display. In one preferred embodiment, the microcontroller 410 generates a continuous display of the concentration of the target substance, this arrangement being particularly useful in the monitoring of the tidal breathing of a patient.

The present invention will be further illustrated by the following specific example.

EXAMPLES

Example 1

An analysis of the water and carbon dioxide content of exhaled breath of a subject was obtained as follows:

The breath exhaled by a subject was analysed for its carbon dioxide content by infrared mass spectroscopy techniques using known techniques and an Oxicap Model 4700 mass spectrometer (commercially available apparatus, Datex-Ohmeda, Louisville, Colo.). The results of the analysis are represented graphically in FIG. 9.

The same breath of the same subject was analysed for water content using a sensor as hereinbefore described and shown in the accompanying figures. The sensor comprises two electrodes with a coating comprising zeolite and nafion, as described. The analysis of the breath was conducted by having the subject breath into a mouthpiece as shown in FIG. 7, in which was installed an electrochemical sensor of the aforementioned construction. The output of the sensor is shown graphically in FIG. 9.

Figure 9:
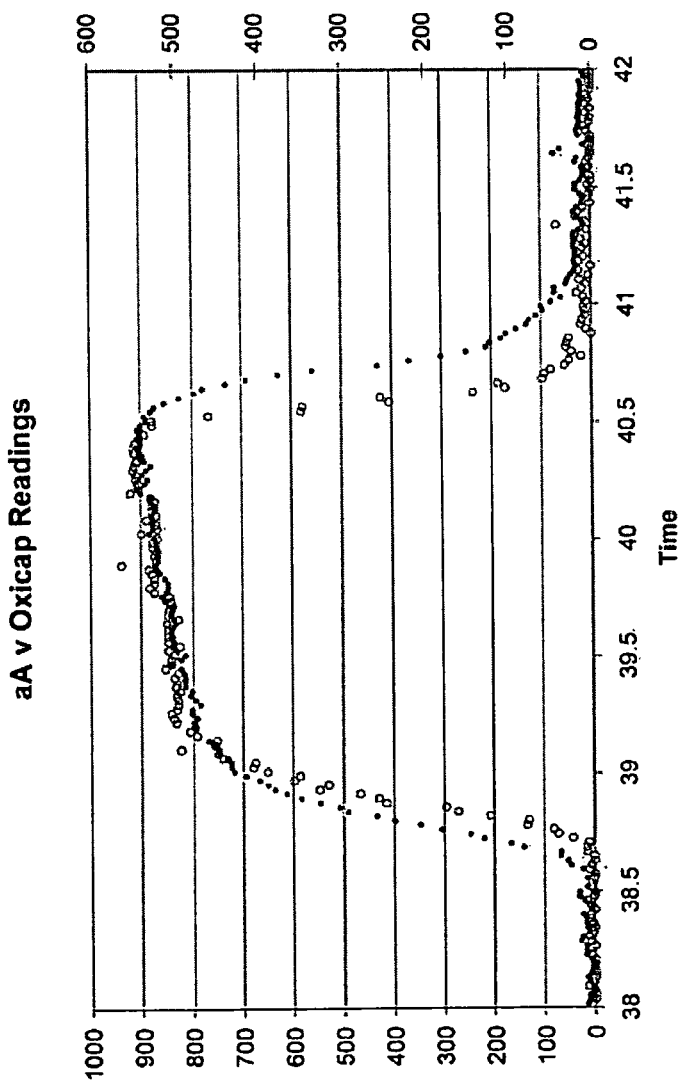
FIG. 9 is a graphical representation of the output from an experiment to measure the water and carbon dioxide content of exhaled breath.

Referring to FIG. 9, the results of the analysis for a single exhaled breath of the subject are shown in the graph. The data points relating to carbon dioxide content are shown in light circles, while those relating to water content are shown in dark circles. The scales of the data points have been adjusted to achieve the best overlay of the two traces. The figure shows that there is a very strict correlation between the water content of the breath with the carbon dioxide concentration, throughout the entire exhaled breath. The profile of the trace has the shape of a typical capnogram, as would be expected when measuring the change in carbon dioxide content throughout the exhaled breath. It can be seen that the profile of the trace for water concentration follows that for carbon dioxide almost exactly throughout the entire breath.

It will be noted that the width of the profile of the two traces is different, with the trace for water being slightly wider than that for carbon dioxide. This difference is explained by the arrangement of conduits used to direct the exhaled breath to the relevant sensor apparatus. As noted, the subject exhaled through a mouthpiece and conduit as shown in FIG. 7. Thus, the electrochemical sensor was placed in the mainstream of the exhaled breath. In order to provide a stream for analysis to the mass spectrometer, a sample of the exhaled breath was taken as a sidestream and pumped to the spectrometer inlet.

It will thus be appreciated, that a knowledge of the concentration of one of carbon dioxide or water in the exhaled breath of a subject and details of the correlation between the two, as shown in FIG. 9, allows the concentration of the other component to be readily determined. This represents a significant finding and offers a significant improvement in the techniques available to measure and analyse the composition of the breath exhaled by a subject. This in turn will greatly assist medical practitioners in diagnosing a range of respiratory disorders.

Example 2

Figure 10:
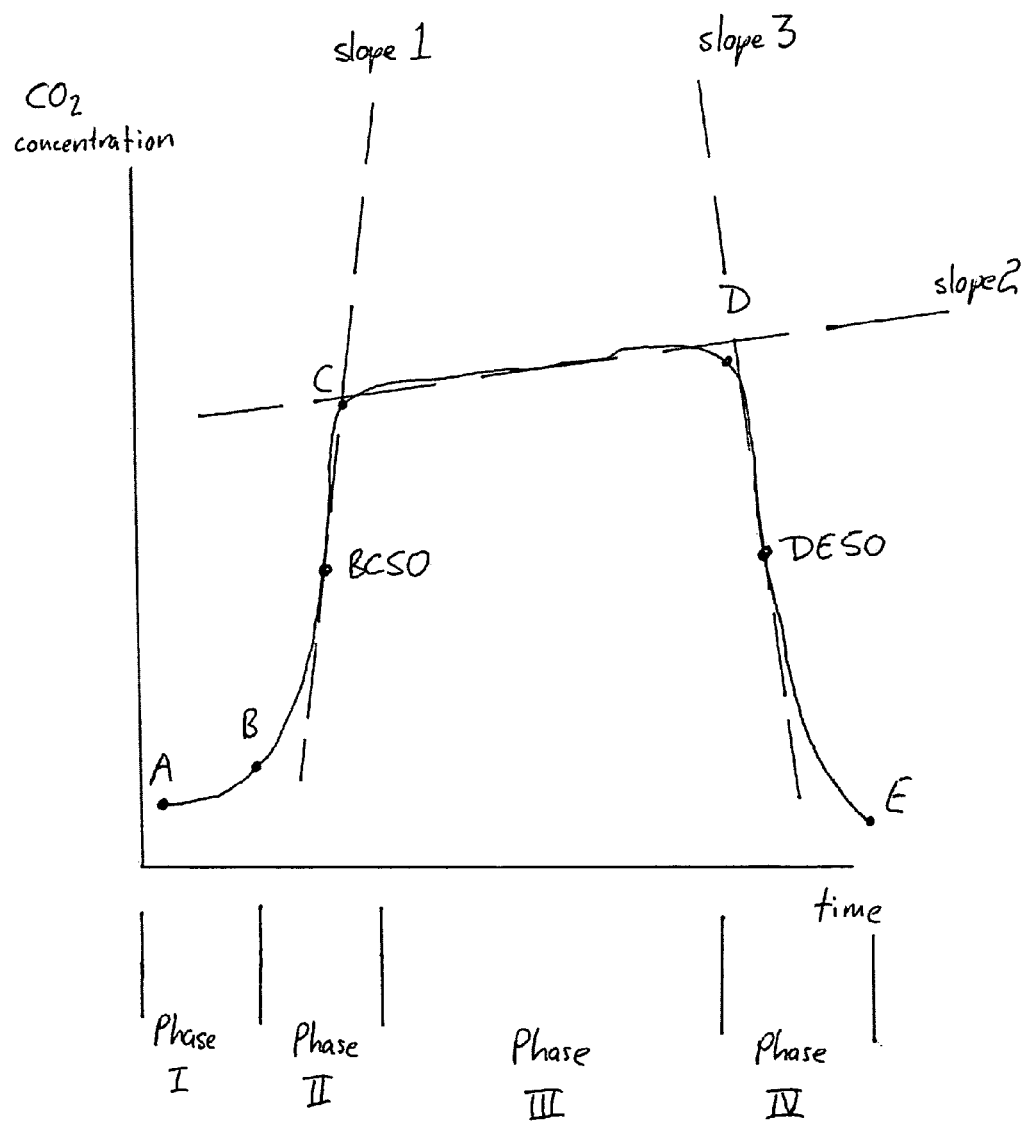
FIG. 10 is a graphical representation of a typical trace of the concentration of carbon dioxide or water vapour in the exhaled gas stream plotted against time.

Referring to FIG. 10, there is shown a graph of carbon dioxide concentration plotted against time obtained from the measurement of the carbon dioxide concentration in an exhaled gas stream throughout the period of the exhalation. This form of graph is known in the art as a 'capnogram'. Similar traces are obtained with other gaseous components in the exhaled gas stream, most notably water vapour. The following analytical techniques may be equally well applied to the similar traces obtained with components other than carbon dioxide.

The trace in FIG. 10 may be characterized as having points of inflection, indicated as points A, B, C, D and E, which generally separate four phases of the trace. Phase I is the volume of carbon dioxide-free gas that is produced at the very start of exhalation by the subject. Phase II is the ascending phase, characterized by a rapid increase in the concentration of carbon dioxide and represents the transition from carbon dioxide-free gas to the early emptying portions of the lung. Phase III is the (alveolar) plateau phase and corresponds to the later emptying portions of the lungs, where the concentration of carbon dioxide continues to slowly rise with time. Point D is generally indicated to be the end-tidal concentration of carbon dioxide ($PetCO_2$). Phase IV of the trace is the final stage, where the carbon dioxide concentration falls rapidly to that of the ambient gas composition.

Two mid-points can be identified, that is BC50, between points B and C, and DE50 between points D and E. These mid-points are used to define data points within the shape analysis.

Slope 1 indicated in FIG. 10 is the gradient of the trace during the ascending phase, Phase II. The slope may be calculated in any suitable manner, for example being the tangent to the curve at the mid-point BC50.

Slope 2 indicated in FIG. 10 is the gradient of the plateau phase, Phase III.

Finally, slope 3 is the gradient of the descending phase, Phase IV. Again, this may be calculated using any suitable technique and, for example may be taken as the tangent to the mid-point DE50.

The region of the trace around Point C generally comprises a 'shoulder' and can be represented mathematically using the general equation 1:

$$Y = \frac{1}{1 + aX^2} \quad (1)$$

where Y is the concentration of carbon dioxide and X is the time.

Figure 11:
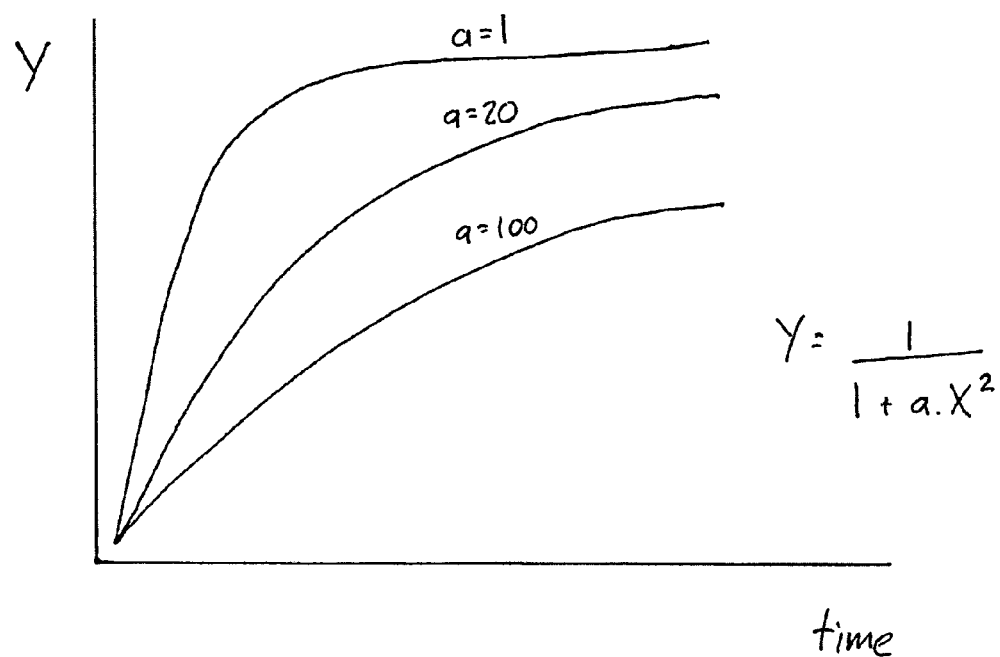
FIG. 11 is a graphical representation of three different traces of the general type of FIG. 10.

The coefficient 'a' in equation 1 determines the shape of the curve and may be used to express the extent to which the trace is curved. The curvature of the shoulder portion varies according to the lung function of the subject. In particular, the trace for normal lung function is provided with a value of a=1. Increasing values of a indicate a reduction in lung function, in particular an increase in breathlessness of the subject. Accordingly, the coefficient a can be used to provide a numerical scale of the extent of breathlessness of the subject. Examples of traces with varying values of coefficient a (a=1, a=20, a=100) are shown in FIG. 11.

The inverse of equation 1 is given by equation 2 as follows:

$$aX^2 = Y' = (1/(Y-1))^{1/2} \quad (2)$$

Equation 2 may be used to linearly transform the trace data, such that standard regression techniques can be applied to provide a best fit line through the data generated in the measurement of the gas concentration and determine the coefficient of the line of best fit. In particular, a graph plotting Y' against time (X) is represented by a straight line, with the gradient of the line being the coefficient a, and best fit analysis can be used to determine the straight line of best fit to the measurement data obtained, and hence the best value of coefficient a. A representative graph of Y' against time (X) is shown in FIG. 12.

Figure 12:
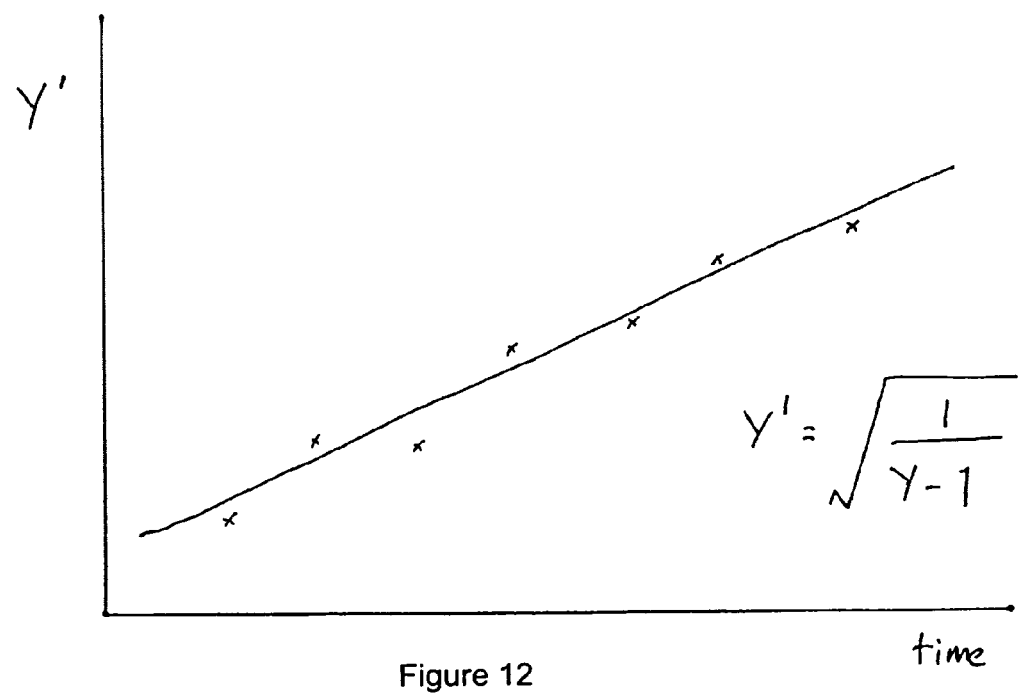
FIG. 12 is a graphical representation of the best fit analysis of the trace of FIG. 10 to determine the coefficient 'a'.

The variation in the actual data points from the line of FIG. 12 can be used to assess the fitting confidence of the coefficient to the acquired data and/or indicate the level of noise in the data.

Other techniques may be used to analyses the acquired data, in particular expressing alternatives to equation 1, as follows:

$$Y = \frac{1}{1 + a \cdot \log X^2} \quad (3)$$

and $$Y = \frac{1}{1 + a \cdot \tan X^2} \quad (4)$$

Example 3

A sensor having the general configuration shown in FIGS. 2 and 3 was prepared. The electrodes were coated with an ion exchange layer comprising a commercially available sulphonated tetrafluoroethylene copolymer (Nafion®, ex Du Pont) and zeolite 4A. The coating was prepared as follows:

A suspension of the zeolite material was suspended in 10 ml of methanol. The zeolite had a uniform range of particle sizes, about 1 micron particle diameter.

The suspension was sonicated for 10 minutes, to ensure even dispersion of the Zeolite within the solution. An ultrasonic bath or probe may also be used. The electrode to be coated was then immersed into the solution and held for 2 seconds before withdrawal. The electrode was laid flat and the solvent allowed to naturally evapourate. Forced air convection may also be used to accelerate the evaporation of the solvent, if necessary.

The electrodes were inspected using scanning electron microscopy (SEM) to determine the distribution of zeolite particles across the electrodes. The results are shown in FIG. 16. As can be seen, the zeolite particles are finely dispersed across the surface of the electrode, with the spacing between particles generally being at least one particle diameter.

With the sensor still in the horizontal position, a minute volume of Nafion polymer was then dispensed onto the surface of the sensor using a syringe, and spread across the entire surface of the sensor using the edge of the syringe needle used to dispense the fluid. The solvent was again left to naturally evaporate away. The volume was such to ensure complete coverage of the surface area of the sensor, and to ensure that the resultant thickness of the film was as small as possible. Typical volumes range from 1 to 10 ul to cover an area of 1 $cm^2$, preferably 2 ul. The resultant thickness of the residual layer (after evaporation of the solvent) should be reasonably thin, consistent with the intended application. Practically, layer thicknesses of 10 to 1000 nm can be achieved using this method, preferably 100 nm.

Figure 17:
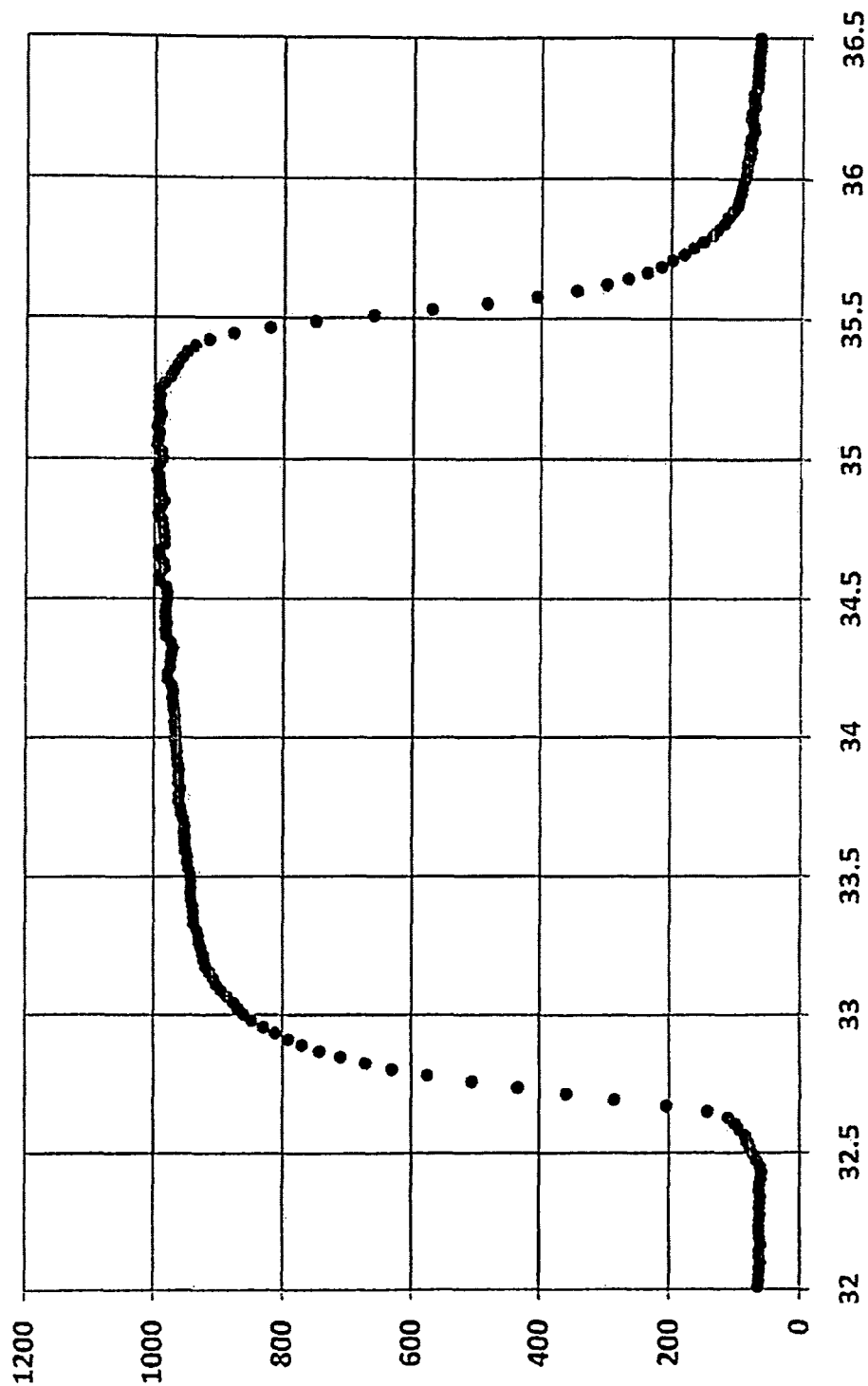
FIG. 17 is a trace of water vapour concentration plotted against time of a gas stream exhaled by a subject measured using the sensor shown in FIG. 16.

The sensor was used to analyse the composition of the breath exhaled by a patient, in particular the water vapour content of the exhaled breath, by having the patient inhale and exhale through the assembly of FIG. 2. The resulting trace of water vapour concentration plotted against time is shown in FIG. 17, from which it can be seen that the sensor produced a very accurate trace of the variation in the concentration of water in the exhaled breath over time.

It has been found that the sensor of this embodiment provides a very fast response to changes in water vapour concentration in the gas stream contacting the sensor element, while at the same time providing an output signal that allows a particularly accurate determination of changes in the water vapour concentration to be made. This in turn allows the sensor to be very specific in its detection of water vapour, thereby providing a means for accurately following the changes in water vapour content of exhaled gas streams of a subject over the short, medium and long term.

The invention claimed is:

1. A method of determining the respiratory function of a subject, the method comprising:
   measuring the concentration of water vapour in the gas stream exhaled by the subject using an electrochemical sensor, wherein said measuring comprises causing the gas stream to impinge on a sensing element of said sensor, the sensing element comprising a working electrode, a counter electrode and a layer of ion exchange material extending between the working electrode and the counter electrode, the ion-exchange layer being configured to form an electrical contact between the working electrode and the counter electrode when exposed to water vapour in said gas stream, and applying a pulsed electric potential across the working electrode and counter electrode whereby the sensor generates an output representative of the change of concentration of water vapour over time in said gas stream;

employing a processor to use the output of the sensor to generate data providing a profile representative of said change of water vapour concentration over time in the exhaled gas stream; and from said profile directly determining the respiratory function of the subject.

2. The method according to claim 1, wherein the concentration of water vapour is measured for the duration of at least one complete exhalation.

3. The method according to claim 2, wherein the concentration of water vapour is measured during tidal breathing by the subject.

4. The method according to claim 1, wherein the exhaled gas stream is exhaled from the mouth of the subject.

5. The method of claim 1, wherein said pulsed potential alternates between a rest potential and a potential above the reaction threshold potential.

6. The method of claim 1, wherein the voltage is pulsed at a frequency of from 1 to 500 Hz.

7. The method of claim 1, wherein
the slope of the ascending phase of the profile is measured and said slope is used to determine the respiratory function of the subject.

8. The method according to claim 7, further comprising measuring the slope of the plateau phase of the profile.

9. The method according to claim 8, wherein the ratio of the slope of the ascending phase and the plateau phase is determined.

10. The method according to claim 1 which further comprises analyzing the portion of the profile in the region of the transition from the ascending phase to the plateau phase and using the results of the analysis to make the determination of the respiratory function of the subject.

11. The method of claim 1 wherein said processor generates a display of said profile.

12. The method according to claim 1 wherein storage means are provided for storing a plurality of pre-existing profiles representative of change of concentration of water vapour over time in an exhaled gas stream and means are provided for comparing the profile thus obtained with one or more pre-existing profiles retrieved from the storage means.

13. The method according to claim 12 wherein said profile is compared with one or more pre-existing such profiles obtained from the subject.

14. The method of claim 12 wherein the means for comparing the profiles comprises display means for displaying a plurality of profiles for visual comparison.

15. The method of claim 1 wherein the ion-exchange material comprises a sulphonated tetrafluoroethylene copolymer.

16. The method of claim 1 wherein said subject is suffering from asthma or chronic obstructive pulmonary (COPD).

* * * * *